(12) United States Patent
Modesitt et al.

(10) Patent No.: US 7,837,696 B2
(45) Date of Patent: Nov. 23, 2010

(54) ARTICULATING SUTURING DEVICE AND METHOD

(75) Inventors: D. Bruce Modesitt, San Carlos, CA (US); Michael Zung, San Jose, CA (US); Michael Barrett, Campbell, CA (US); Bernard H. Andreas, Fremont, CA (US); Lewis Isbell, Union City, CA (US)

(73) Assignee: Abbott Laboratories, Abbott Park, IL (US)

( * ) Notice: Subject to any disclaimer, the term of this patent is extended or adjusted under 35 U.S.C. 154(b) by 789 days.

(21) Appl. No.: 10/729,541

(22) Filed: Dec. 5, 2003

(65) Prior Publication Data

US 2004/0122449 A1 Jun. 24, 2004

Related U.S. Application Data

(60) Continuation of application No. 09/651,344, filed on Aug. 29, 2000, now Pat. No. 7,001,400, which is a division of application No. 09/262,402, filed on Mar. 4, 1999, now Pat. No. 6,136,010.

(51) Int. Cl.
*A61B 17/04* (2006.01)
(52) U.S. Cl. .................. 606/144; 606/139; 606/148
(58) Field of Classification Search ............... 606/139, 606/144, 145, 148, 150, 153, 213, 192; 128/898; 604/164.13

See application file for complete search history.

(56) References Cited

U.S. PATENT DOCUMENTS 312,408 A 2/1885 Wackerhagen (Continued)

FOREIGN PATENT DOCUMENTS

DE 912619 5/1954

(Continued)

OTHER PUBLICATIONS

U.S. Appl. No. 10/357,984, Mail Date Nov. 14, 2007, Office Action.

(Continued)

*Primary Examiner*—Julian W Woo
(74) *Attorney, Agent, or Firm*—Workman Nydegger

(57) ABSTRACT

Devices, systems, and methods for suturing of body lumens allow the suturing of vascular puncture sites located at the distal end of a percutaneous tissue tract. An elongated articulated foot near a distal end of a shaft is inserted through the penetration and actuated so that the foot extends along the lumenal axis. The foot carries suturing attachment cuffs, and needles are advanced from the shaft through the vessel wall outside of the penetration and into engagement with the needle cuffs after the foot has been drawn proximally up against the endothelial surface of the blood vessel. The cross-section of the shaft within the tissue tract can be minimized by laterally deflecting the needles as they leave the shaft, while tapered depressions within the foot can guide the advancing needles into engagement with the cuffs. The cuffs lockingly engage the needles and can be withdrawn proximally along the needle paths and through the tissue tract so as to form a loop of suture across the puncture. The articulating foot may be realigned with the shaft and withdrawn proximally through the tissue tract without dilating the tissue tract.

30 Claims, 14 Drawing Sheets

U.S. PATENT DOCUMENTS

| | | | |
|---|---|---|---|
| 659,422 A | 10/1900 | Shidler |
| 1,625,602 A | 4/1927 | Gould et al. |
| 2,012,776 A | 8/1935 | Roeder |
| 2,127,903 A | 8/1938 | Bowen |
| 2,371,978 A | 3/1945 | Perham |
| 2,397,823 A | 4/1946 | Walter |
| RE22,857 E | 3/1947 | Ogburn |
| 2,646,045 A | 7/1953 | Priestley |
| 2,941,489 A | 6/1960 | Fischbein |
| 2,959,172 A | 11/1960 | Held |
| 3,104,666 A | 9/1963 | Hale et al. |
| 3,197,102 A | 7/1965 | Bates et al. |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,820,544 A | 6/1974 | Semm |
| 3,840,017 A | 10/1974 | Violante |
| 3,874,388 A | 4/1975 | King et al. |
| 3,926,194 A | 12/1975 | Greenberg et al. |
| 3,939,820 A | 2/1976 | Grayzel |
| 3,985,138 A | 10/1976 | Jarvik |
| 4,018,228 A | 4/1977 | Goosen |
| 4,109,658 A | 8/1978 | Hughes |
| 4,128,100 A | 12/1978 | Wendorff |
| 4,161,951 A | 7/1979 | Scanlan, Jr. |
| 4,168,073 A | 9/1979 | LaRue |
| 4,182,339 A | 1/1980 | Hardy, Jr. |
| 4,216,776 A | 8/1980 | Downie et al. |
| 4,235,177 A | 11/1980 | Arbuckle |
| 4,235,238 A | 11/1980 | Ogiu et al. |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,493,323 A | 1/1985 | Albright et al. |
| 4,553,543 A | 11/1985 | Amarasinghe |
| 4,587,969 A | 5/1986 | Gillis |
| 4,596,559 A | 6/1986 | Fleischhacker |
| 4,629,450 A | 12/1986 | Suzuki et al. |
| 4,651,733 A | 3/1987 | Mobin-Uddin |
| 4,723,549 A | 2/1988 | Wholey et al. |
| 4,738,666 A | 4/1988 | Fuqua |
| 4,744,364 A * | 5/1988 | Kensey ............... 606/213 |
| 4,748,982 A * | 6/1988 | Horzewski et al. .......... 606/192 |
| 4,803,984 A | 2/1989 | Narayanan et al. |
| 4,836,205 A | 6/1989 | Barrett |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yoon |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,109,780 A | 5/1992 | Slouf et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,171,251 A | 12/1992 | Bregen et al. |
| 5,178,629 A | 1/1993 | Kammerer |
| 5,192,294 A | 3/1993 | Blake, III |
| 5,192,302 A | 3/1993 | Kensey et al. |
| 5,211,650 A | 5/1993 | Noda |
| 5,217,470 A | 6/1993 | Weston |
| 5,217,485 A | 6/1993 | Liv et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,242,427 A | 9/1993 | Bilweis |
| 5,250,033 A | 10/1993 | Evans et al. |
| 5,250,053 A | 10/1993 | Snyder |
| 5,254,105 A | 10/1993 | Haaga |
| 5,254,126 A | 10/1993 | Filipi et al. |
| 5,258,003 A | 11/1993 | Ciaglia et al. |
| 5,259,846 A | 11/1993 | Granger et al. |
| 5,279,311 A | 1/1994 | Snyder |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,292,309 A | 3/1994 | VanTassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |
| 5,330,445 A | 7/1994 | Haaga |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,354,312 A | 10/1994 | Brinkerhoff et al. |
| 5,364,407 A | 11/1994 | Poll |
| 5,364,408 A | 11/1994 | Gordon |
| 5,368,601 A | 11/1994 | Sauer et al. |
| 5,374,275 A | 12/1994 | Bradley et al. |
| 5,374,278 A | 12/1994 | Chesterfield et al. |
| 5,376,096 A | 12/1994 | Foster |
| 5,383,896 A | 1/1995 | Gershony et al. |
| 5,387,221 A | 2/1995 | Bisgaard |
| 5,387,227 A | 2/1995 | Grice |
| 5,391,176 A | 2/1995 | de la Torre |
| 5,391,182 A | 2/1995 | Chin |

| | | | | | | |
|---|---|---|---|---|---|---|
| 5,395,332 A | 3/1995 | Ressemann et al. | | 5,700,273 A | 12/1997 | Buelna et al. |
| 5,395,349 A | 3/1995 | Quiachon et al. | | 5,707,379 A | 1/1998 | Fleenor et al. |
| 5,397,325 A | 3/1995 | Delia Badia et al. | | 5,713,910 A | 2/1998 | Gordon et al. |
| 5,403,329 A | 4/1995 | Hinchcliffe | | 5,716,369 A | 2/1998 | Riza |
| 5,403,331 A | 4/1995 | Chesterfield et al. | | 5,720,757 A | 2/1998 | Hathaway et al. |
| 5,403,338 A | 4/1995 | Milo | | 5,725,552 A | 3/1998 | Kotula et al. |
| 5,411,481 A | 5/1995 | Allen et al. | | 5,728,109 A | 3/1998 | Schulze et al. |
| 5,413,571 A | 5/1995 | Katsaros et al. | | 5,728,114 A | 3/1998 | Evans et al. |
| 5,417,699 A | 5/1995 | Klein et al. | | 5,728,133 A | 3/1998 | Kontos |
| 5,425,705 A | 6/1995 | Evard et al. | | 5,728,151 A | 3/1998 | Garrison et al. |
| 5,425,740 A | 6/1995 | Hutchinson, Jr. | | 5,741,276 A | 4/1998 | Poloyko et al. |
| 5,431,666 A | 7/1995 | Sauer et al. | | 5,741,280 A | 4/1998 | Fleenor |
| 5,433,700 A | 7/1995 | Peters | | 5,746,755 A | 5/1998 | Wood et al. |
| 5,452,733 A | 9/1995 | Sterman et al. | | 5,749,890 A * | 5/1998 | Shaknovich ................ 128/898 |
| 5,454,822 A | 10/1995 | Schob et al. | | 5,755,727 A | 5/1998 | Kontos |
| 5,454,834 A | 10/1995 | Boebel et al. | | 5,759,188 A | 6/1998 | Yoon |
| 5,458,574 A | 10/1995 | Machold et al. | | 5,766,183 A | 6/1998 | Sauer |
| 5,464,426 A | 11/1995 | Bonutti | | 5,766,186 A | 6/1998 | Faraz et al. |
| 5,466,241 A | 11/1995 | Leroy et al. | | 5,766,217 A | 6/1998 | Christy |
| 5,470,338 A | 11/1995 | Whitfield et al. | | 5,769,862 A | 6/1998 | Kammerer et al. |
| 5,476,469 A | 12/1995 | Hathaway et al. | | 5,779,719 A | 7/1998 | Klein et al. |
| 5,476,470 A | 12/1995 | Fitzgibbons, Jr. | | 5,782,860 A | 7/1998 | Epstein et al. |
| 5,478,309 A | 12/1995 | Sweezer et al. | | 5,782,861 A | 7/1998 | Cragg et al. |
| 5,478,353 A | 12/1995 | Yoon | | 5,792,151 A | 8/1998 | Heck et al. |
| 5,480,407 A | 1/1996 | Wan et al. | | 5,797,928 A | 8/1998 | Kogasaka |
| 5,486,190 A | 1/1996 | Green | | 5,799,661 A | 9/1998 | Boyd et al. |
| 5,489,295 A | 2/1996 | Piplani et al. | | 5,810,849 A | 9/1998 | Kontos |
| 5,496,332 A | 3/1996 | Sierra et al. | | 5,810,850 A | 9/1998 | Hathaway et al. |
| 5,507,744 A | 4/1996 | Tay et al. | | 5,817,113 A | 10/1998 | Gifford, III et al. |
| 5,507,755 A | 4/1996 | Gresl et al. | | 5,820,631 A | 10/1998 | Nobles |
| 5,507,757 A | 4/1996 | Sauer et al. | | 5,824,010 A | 10/1998 | McDonald |
| 5,507,758 A | 4/1996 | Thomason et al. | | 5,836,955 A | 11/1998 | Buelna et al. |
| 5,509,902 A | 4/1996 | Raulerson | | 5,836,956 A | 11/1998 | Buelna et al. |
| 5,520,665 A | 5/1996 | Fleetwood | | 5,846,253 A | 12/1998 | Buelna et al. |
| 5,520,702 A | 5/1996 | Sauer et al. | | 5,855,585 A | 1/1999 | Kontos |
| 5,527,321 A | 6/1996 | Hinchliffe | | 5,860,990 A | 1/1999 | Nobles et al. |
| 5,527,322 A | 6/1996 | Klein et al. | | 5,860,991 A | 1/1999 | Klein et al. |
| D372,310 S | 7/1996 | Hartnett | | 5,861,005 A | 1/1999 | Kontos |
| 5,531,700 A * | 7/1996 | Moore et al. ........... 604/164.13 | | 5,871,490 A | 2/1999 | Schulze et al. |
| 5,536,273 A | 7/1996 | Lehrer | | 5,871,502 A | 2/1999 | Suryadevara |
| 5,540,701 A | 7/1996 | Sharkey et al. | | 5,873,876 A | 2/1999 | Christy |
| 5,540,704 A | 7/1996 | Gordon et al. | | 5,876,411 A | 3/1999 | Kontos |
| 5,545,171 A | 8/1996 | Sharkey et al. | | 5,897,487 A | 4/1999 | Ouchi |
| 5,545,178 A | 8/1996 | Kensey et al. | | 5,897,564 A | 4/1999 | Schulze et al. |
| 5,545,180 A | 8/1996 | Le et al. | | 5,902,311 A | 5/1999 | Andreas et al. |
| 5,549,618 A | 8/1996 | Fleenor et al. | | 5,904,697 A | 5/1999 | Gifford, III et al. |
| 5,549,631 A | 8/1996 | Bonutti | | 5,906,631 A | 5/1999 | Imran |
| 5,554,162 A | 9/1996 | DeLange | | 5,919,207 A | 7/1999 | Taheri |
| 5,562,684 A | 10/1996 | Kammerer | | 5,928,266 A * | 7/1999 | Kontos ....................... 606/213 |
| 5,562,686 A | 10/1996 | Sauer et al. | | 5,951,590 A | 9/1999 | Goldfarb |
| 5,562,688 A | 10/1996 | Riza | | 5,954,732 A | 9/1999 | Hart et al. |
| 5,562,728 A | 10/1996 | Lazarus et al. | | 5,957,936 A | 9/1999 | Yoon et al. |
| 5,569,271 A | 10/1996 | Hoel | | 5,957,937 A | 9/1999 | Yoon |
| 5,571,120 A | 11/1996 | Yoon | | 5,957,938 A | 9/1999 | Zhu et al. |
| 5,573,540 A | 11/1996 | Yoon | | 5,964,773 A | 10/1999 | Greenstein |
| 5,584,842 A | 12/1996 | Fogarty et al. | | 5,964,782 A | 10/1999 | Lafontaine et al. |
| 5,591,177 A | 1/1997 | Lehrer | | 5,976,161 A | 11/1999 | Kirsch et al. |
| 5,591,179 A | 1/1997 | Edelstein | | 5,980,539 A | 11/1999 | Kontos |
| 5,591,206 A | 1/1997 | Moufarrege | | 5,997,555 A | 12/1999 | Kontos |
| 5,593,421 A | 1/1997 | Bauer | | 6,001,109 A | 12/1999 | Kontos |
| 5,603,718 A | 2/1997 | Xu | | 6,022,372 A | 2/2000 | Kontos |
| 5,609,597 A | 3/1997 | Lehrer | | 6,024,747 A | 2/2000 | Kontos |
| 5,611,794 A | 3/1997 | Sauer et al. | | 6,036,699 A * | 3/2000 | Andreas et al. ............. 606/139 |
| 5,613,974 A | 3/1997 | Andreas et al. | | 6,042,601 A | 3/2000 | Smith |
| 5,613,975 A | 3/1997 | Christy | | 6,048,351 A | 4/2000 | Gordon et al. |
| 5,626,588 A | 5/1997 | Sauer et al. | | 6,048,354 A | 4/2000 | Lawrence |
| 5,643,289 A | 7/1997 | Sauer et al. | | 6,048,357 A | 4/2000 | Kontos |
| 5,643,295 A | 7/1997 | Yoon | | 6,077,276 A | 6/2000 | Kontos |
| 5,643,318 A | 7/1997 | Tsukernik et al. | | 6,077,279 A | 6/2000 | Kontos |
| 5,649,959 A | 7/1997 | Hannam et al. | | 6,117,144 A | 9/2000 | Nobles et al. |
| 5,662,664 A | 9/1997 | Gordon et al. | | 6,126,675 A | 10/2000 | Shchervinsky et al. |
| 5,669,917 A | 9/1997 | Sauer et al. | | 6,132,439 A | 10/2000 | Kontos |
| 5,676,689 A | 10/1997 | Kensey et al. | | 6,132,440 A | 10/2000 | Hathaway et al. |

| | | |
|---|---|---|
| 6,136,010 A | 10/2000 | Modesitt et al. |
| 6,139,556 A | 10/2000 | Kontos |
| 6,152,936 A | 11/2000 | Christy et al. |
| 6,165,204 A | 12/2000 | Levinson et al. |
| 6,197,042 B1 | 3/2001 | Ginn et al. |
| 6,245,079 B1 | 6/2001 | Nobles et al. |
| 6,248,124 B1 | 6/2001 | Pedros et al. |
| 6,296,657 B1 | 10/2001 | Brucker |
| 6,348,059 B1 | 2/2002 | Hathaway et al. |
| 6,358,258 B1 | 3/2002 | Arcia et al. |
| 6,395,015 B1 | 5/2002 | Borst et al. |
| 6,428,472 B1 | 8/2002 | Haas |
| 6,428,549 B1 | 8/2002 | Kontos |
| 6,436,109 B1 | 8/2002 | Kontos |
| 6,443,963 B1 | 9/2002 | Baldwin et al. |
| 6,451,031 B1 | 9/2002 | Kontos |
| 6,511,489 B2 | 1/2003 | Field et al. |
| 6,517,553 B2 * | 2/2003 | Klein et al. ............... 606/144 |
| 6,533,812 B2 | 3/2003 | Swanson et al. |
| 6,562,052 B2 | 5/2003 | Nobles et al. |
| 6,569,185 B2 | 5/2003 | Ungs |
| 6,572,629 B2 | 6/2003 | Kalloo et al. |
| 6,610,072 B1 | 8/2003 | Christy et al. |
| 6,623,509 B2 | 9/2003 | Ginn |
| 6,623,510 B2 | 9/2003 | Carly et al. |
| 6,632,237 B2 | 10/2003 | Ben-David et al. |
| 6,641,592 B1 | 11/2003 | Sauer et al. |
| 6,663,655 B2 | 12/2003 | Ginn et al. |
| 6,676,685 B2 | 1/2004 | Pedros et al. |
| 6,695,867 B2 | 2/2004 | Ginn et al. |
| 6,716,228 B2 | 4/2004 | Tal |
| 6,743,195 B2 | 6/2004 | Zucker |
| 6,743,259 B2 | 6/2004 | Ginn |
| 6,749,621 B2 | 6/2004 | Pantages et al. |
| 6,749,622 B2 | 6/2004 | McGuckin, Jr. et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,692 B2 | 5/2005 | Ginn et al. |
| 6,911,034 B2 | 6/2005 | Nobles et al. |
| 6,939,357 B2 | 9/2005 | Navarro et al. |
| 6,964,668 B2 | 11/2005 | Modesitt et al. |
| 6,969,397 B2 | 11/2005 | Ginn |
| 7,001,400 B1 | 2/2006 | Modesitt et al. |
| 7,063,710 B2 | 6/2006 | Takamoto et al. |
| 7,083,635 B2 | 8/2006 | Ginn |
| 7,112,225 B2 | 9/2006 | Ginn |
| 7,160,309 B2 | 1/2007 | Voss |
| 7,235,087 B2 | 6/2007 | Modesitt et al. |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| 7,361,183 B2 | 4/2008 | Ginn |
| 7,361,185 B2 | 4/2008 | O'Malley et al. |
| 7,393,363 B2 | 7/2008 | Ginn |
| 7,462,188 B2 | 12/2008 | McIntosh |
| 2001/0046518 A1 | 11/2001 | Sawhney |
| 2002/0099389 A1 | 7/2002 | Michler et al. |
| 2002/0106409 A1 | 8/2002 | Sawhney et al. |
| 2002/0177876 A1 | 11/2002 | Roby et al. |
| 2003/0093093 A1 | 5/2003 | Modesitt et al. |
| 2004/0009205 A1 | 1/2004 | Sawhney |
| 2004/0092964 A1 | 5/2004 | Modesitt et al. |
| 2004/0093027 A1 | 5/2004 | Fabisiak et al. |
| 2004/0097978 A1 | 5/2004 | Modesitt et al. |
| 2004/0127940 A1 | 7/2004 | Ginn et al. |
| 2004/0143290 A1 | 7/2004 | Brightbill |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0191277 A1 | 9/2004 | Sawhney et al. |
| 2004/0210251 A1 | 10/2004 | Kontos |
| 2004/0215232 A1 | 10/2004 | Belhe et al. |
| 2004/0225301 A1 | 11/2004 | Roop et al. |
| 2004/0267193 A1 | 12/2004 | Bagaoisan et al. |
| 2004/0267308 A1 | 12/2004 | Bagaoisan et al. |
| 2005/0059982 A1 | 3/2005 | Zung et al. |
| 2005/0070923 A1 | 3/2005 | McIntosh |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0121042 A1 | 6/2005 | Belhe et al. |
| 2005/0143761 A1 | 6/2005 | Modesitt |
| 2005/0149117 A1 | 7/2005 | Khosravi et al. |
| 2005/0177189 A1 | 8/2005 | Ginn et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0273137 A1 | 12/2005 | Ginn |
| 2006/0034930 A1 | 2/2006 | Khosravi et al. |
| 2006/0047313 A1 | 3/2006 | Khanna et al. |
| 2006/0079914 A1 | 4/2006 | Modesitt |
| 2006/0100664 A1 | 5/2006 | Pai et al. |
| 2006/0142785 A1 | 6/2006 | Modesitt |
| 2006/0253037 A1 | 11/2006 | Ginn et al. |
| 2006/0253072 A1 | 11/2006 | Pai et al. |
| 2007/0049967 A1 | 3/2007 | Sibbitt, Jr. et al. |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0112304 A1 | 5/2007 | Voss |
| 2007/0123817 A1 | 5/2007 | Khosravi et al. |
| 2007/0167959 A1 | 7/2007 | Modesitt |
| 2007/0203506 A1 | 8/2007 | Sibbitt, Jr. et al. |
| 2008/0009794 A1 | 1/2008 | Bagaoisan et al. |
| 2008/0065151 A1 | 3/2008 | Ginn |
| 2008/0065152 A1 | 3/2008 | Carley |
| 2009/0048615 A1 | 2/2009 | McIntosh |
| 2009/0088779 A1 | 4/2009 | Zung et al. |

FOREIGN PATENT DOCUMENTS

| | | |
|---|---|---|
| DE | 4210724 C1 | 7/1993 |
| DE | 9217932 U1 | 7/1993 |
| DE | 4220283 | 12/1993 |
| DE | 10211360 | 10/2003 |
| EP | 0 140 557 | 5/1985 |
| EP | 0 207 545 | 1/1987 |
| EP | 0 474 887 | 3/1992 |
| EP | 0 478 358 | 4/1992 |
| EP | 0 589 409 | 9/1992 |
| EP | 0 624 343 | 4/1993 |
| EP | 0 542 126 | 5/1993 |
| EP | 0 568 098 | 11/1993 |
| EP | 0 669 101 | 8/1995 |
| EP | 0 669 102 | 8/1995 |
| EP | 0 669 103 | 8/1995 |
| EP | 0 812 571 | 3/1997 |
| EP | 0 941 698 | 9/1999 |
| FR | 1059544 | 3/1954 |
| FR | 2768324 | 3/1999 |
| JP | 2119866 A | 5/1990 |
| JP | 542161 A | 2/1993 |
| SU | 820810 | 4/1981 |
| SU | 993922 | 2/1983 |
| SU | 1093329 | 5/1984 |
| SU | 1174036 | 8/1985 |
| SU | 1544383 | 2/1990 |
| SU | 1648400 | 5/1991 |
| WO | WO 94/05213 | 3/1994 |
| WO | WO 94/27503 | 12/1994 |
| WO | WO 94/28801 | 12/1994 |
| WO | WO 95/05121 | 2/1995 |
| WO | WO 95/25468 | 9/1995 |

| | | |
|---|---|---|
| WO | WO 95/35065 | 12/1995 |
| WO | WO 97/00046 | 1/1997 |
| WO | WO 97/03613 | 2/1997 |
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 00/12013 | 3/2000 |
| WO | WO 00/51498 | 9/2000 |
| WO | WO02/062234 | 8/2002 |
| WO | WO03/094748 | 11/2003 |
| WO | WO 03/099134 | 12/2003 |
| WO | WO2005/000126 | 1/2005 |
| WO | WO 2005/023119 | 3/2005 |
| WO | WO 2005/025430 | 3/2005 |
| WO | WO 2005/030060 | 4/2005 |
| WO | WO2005/041782 | 5/2005 |
| WO | WO2005/063129 | 7/2005 |
| WO | WO2005/092204 | 10/2005 |
| WO | WO2005/112782 | 12/2005 |
| WO | WO2006/026116 | 3/2006 |
| WO | WO2006/052611 | 5/2006 |
| WO | WO2006/052612 | 5/2006 |
| WO | WO2006/078578 | 7/2006 |
| WO | WO2006/115901 | 11/2006 |
| WO | WO2006/115904 | 11/2006 |
| WO | WO2006/118877 | 11/2006 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/81836 | 7/2007 |
| WO | WO 2010/031050 | 3/2010 |

OTHER PUBLICATIONS

U.S. Appl. No. 10/909,531, Mail Date Dec. 26, 2007, Office Action.
U.S. Appl. No. 11/273,107, Mail Date Jan. 18, 2008, Office Action.
U.S. Appl. No. 11/363,005, Mail Date Dec. 14, 2007, Office Action.
U.S. Appl. No. 11/363,005, Mail Date Apr. 17, 2008, Office Action.
U.S. Appl. No. 12/334,085, filed Dec. 12, 2008, Zung et al.
U.S. Appl. No. 10/660,288, Mail Date Apr. 29, 2009, Office Action.
U.S. Appl. No. 10/909 531, Mail Date Jun. 13, 2008, Office Action.
U.S. Appl. No. 10/909,531, Mail Date Feb. 9, 2009, Office Action.
U.S. Appl. No. 11/273,107, Mail Date Sep. 5, 2008, Office Action.
U.S. Appl. No. 11/273,107, Mail Date Apr. 9, 2009, Office Action.
U.S. Appl. No. 11/363,005, Mail Date Dec. 23, 2008, Office Action.
U.S. Appl. No. 11/363,005, Mail Date Jul. 10, 2009, Notice Of Allowance.
U.S. Appl. No. 90/006,469, Mail Date Nov. 29, 2002, Request for Re-Examination.
U.S. Appl. No. 90/006,469, Mail Date Sep. 10, 2004, Re-Examination Office Action.
U.S. Appl. No. 90/006,469, Mail Date Sep. 27, 2005, Notice of Intent.
U.S. Appl. No. 90/006,469, Mail Date Jun. 27, 2006, Re-Examination Certification.
U.S. Appl. No. 10/357,984, filed Feb. 4, 2003, Modesett et al.
U.S. Appl. No. 11/465,527, filed Aug. 18, 2006, Dawn Ma.
U.S. Appl. No. 11/891,358, filed Aug. 9, 2007.
U.S. Appl. No. 11/891,513, filed Aug. 9, 2007.
U.S. Appl. No. 90/006,469, filed Nov. 29, 2002, Modesitt.
Elgin National Watch Company, Product Brochure entitled "Elgiloy, A Cobalt Nickel Spring Alloy", 33 pages, (1959).
Faulkner, Catherine B., Letter regarding "VasoSeal Vascular Hemostasis", *Datascope*, New Jersey, 1 page, (1991).
Laurus Medical Corporation, "Endoscopic Suturing Made Simple", The Laurus ND-2600 Needle Driver, Irvine, CA. 1 page, (1994).
Marshall, A.C. & Lock, J.E.; "Structural and compliant anatomy of the patient foramen ovale in patients undergoing transcatheter closure", Am. Heart Journal, 140(2):303-307 (2000).
The Laurus In-Line Endoscopic Suturing Device (Oct. 1994) 1 page.
U.S. Appl. No. 60/711,279, filed Aug. 24, 2005, Sibbitt, Jr. et al.
U.S. Appl. No. 60/726,985, filed Oct. 14, 2005, Sibbitt, Jr. et al.
Grossman, William (edited by) Cardiac Catheterization and Angiography, 3rd Ed., Lea & Febiger, Philadelphia 1986.
Nakamura, S. et al., Techniques for Palmaz-Schatz Stent Deployment in Lesions With a Large Side Branch, *Catheterization and Cardiovascular Diagnosis*, 34: 353-361, 1995.
Serruys, Pw et al., A Comparision of Balloon-Expandable-Stent Implantaion With Balloon Angioplast in Patients With Coronary Artery Disease, *New England Journal of Medicine,* 331:489-495, 1994.
U.S. Appl. No. 10/660,288, filed Mar. 30, 2010, Office Action.
U.S. Appl. No. 10/909,531, filed Apr. 29, 2010, Notice of Allowance.
U.S. Appl. No. 11/465,527, filed Feb. 3, 2010, Office Action.
U.S. Appl. No. 11/508,656, filed Mar. 25, 2010, Office Action.
U.S. Appl. No. 11/508,662, filed Apr. 14, 2010, Office Action.
U.S. Appl. No. 11/508,715, filed Apr. 26, 2010, Office Action.
U.S. Appl. No. 11/552,593, filed Mar. 22, 2010, Notice of Allowance.
U.S. Appl. No. 11/688,722, filed Mar. 10, 2010, Office Action.
U.S. Appl. No. 11/891,358, filed Apr. 26, 2010, Office Action.
U.S. Appl. No. 11/891,513, filed Apr. 9, 2010, Office Action.
U.S. Appl. No. 12/365,397, filed Feb. 4, 2009, Sibbitt, Jr. et al.
U.S. Appl. No. 12/559,377, filed Sep. 14, 2009, Sibbitt, Jr. et al.
International Search Report for PCT/US06/33033 dated Sep. 28, 2007.
International Search Report for PCT/US06/33031 dated May 19, 2008.
International Search Report for PCT/US06/33032 dated Sep. 27, 2007.
U.S. Appl. No. 10/335,147, filed Dec. 13, 2005, Office Action.
U.S. Appl. No. 10/335,147, filed Apr. 17, 2006, Office Action.
U.S. Appl. No. 10/335,147, filed Oct. 4, 2006, Notice of Allowance.
U.S. Appl. No. 10/335,147, filed Dec. 20, 2006, Issue Notification.
U.S. Appl. No. 10/660,288, filed Aug. 3, 2009, Office Action.
U.S. Appl. No. 10/909,531, filed Sep. 16, 2009, Office Action.
U.S. Appl. No. 11/273,107, filed Oct. 28, 2009, Office Action.
U.S. Appl. No. 11/316,775, filed Apr. 16, 2008, Office Action.
U.S. Appl. No. 11/316,775, filed Aug. 6, 2008, Office Action.
U.S. Appl. No. 11/363,005, filed Jan. 14, 2010, Notice of Allowance.
U.S. Appl. No. 11/508,656, filed Dec. 9, 2009, Restriction Requirement.
U.S. Appl. No. 11/508,662, filed Dec. 28, 2009, Restriction Requirement.
U.S. Appl. No. 11/508,715, filed Jan. 6, 2010, Restriction Requirement.
U.S. Appl. No. 11/552,593, filed Aug. 21, 2008, Office Action.
U.S. Appl. No. 11/552,593, filed Feb. 5, 2009, Office Action.
U.S. Appl. No. 11/552,593, filed Oct. 13, 2009, Notice of Allowance.

* cited by examiner

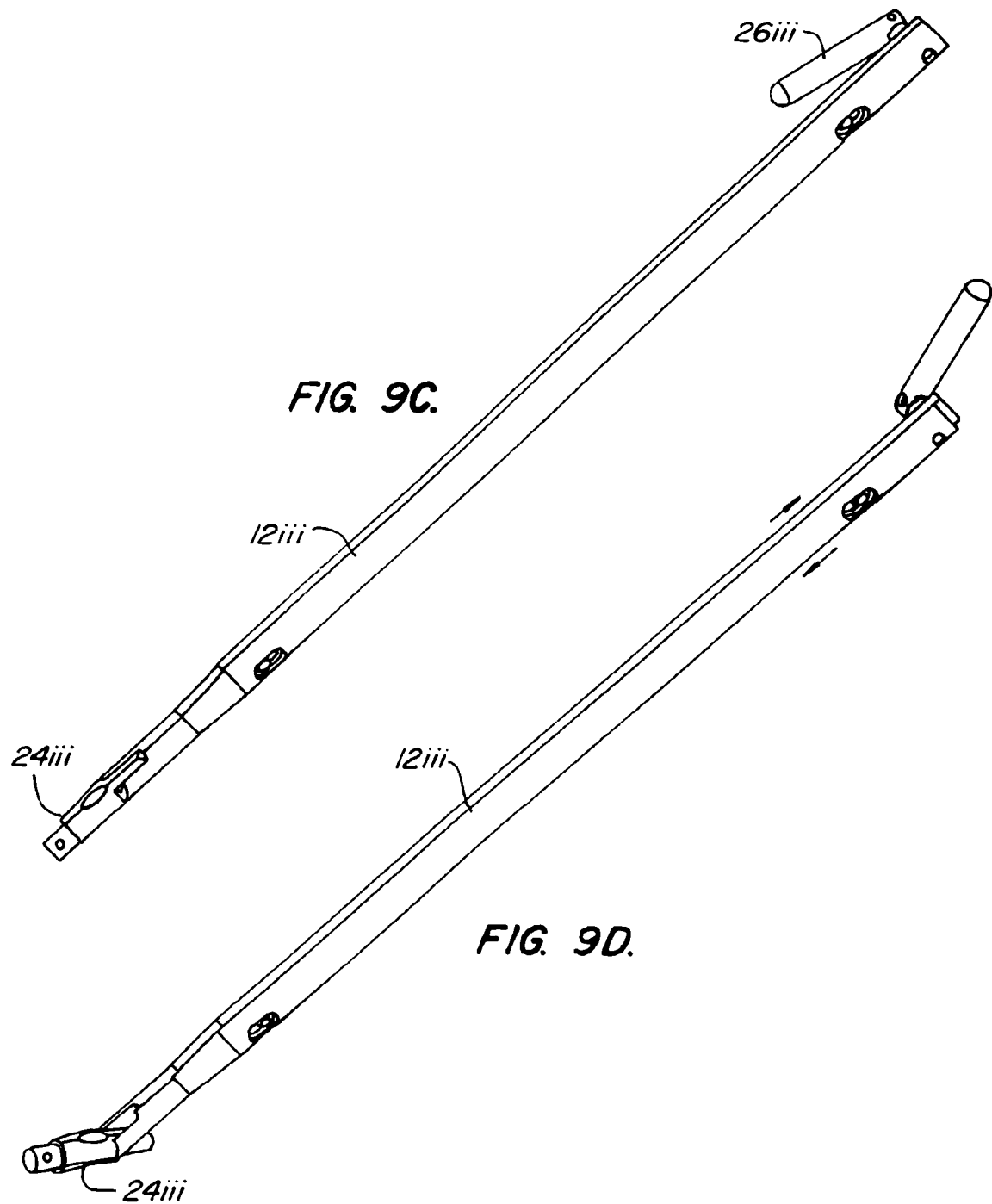

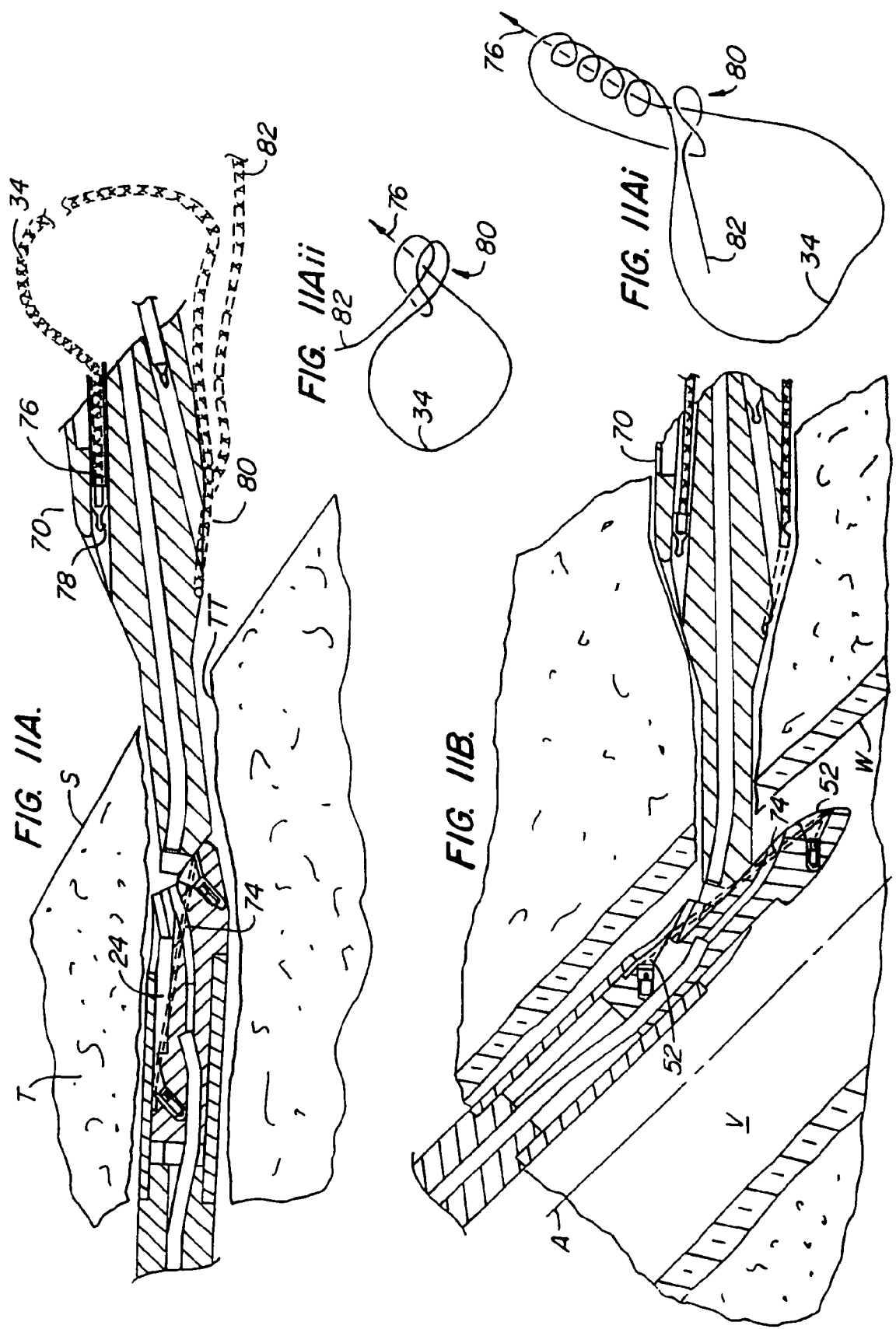

ARTICULATING SUTURING DEVICE AND METHOD

This application is a continuation of, and claims the benefit of priority from application Ser. No. 09/651,344 filed on Aug. 29, 2000, now U.S. Pat. No. 7,001,400, which is a divisional application of application Ser. No. 09/262,402 filed on Mar. 4, 1999, now U.S. Pat. No. 6,136,010. Prior application Ser. Nos. 09/651,344 and 09/262,402 are hereby incorporated herein by reference.

BACKGROUND OF THE INVENTION

1. Field of the Invention

The present invention relates generally to apparatus and methods for the suturing of body lumens. More particularly, the present invention relates to techniques for percutaneous closure of arterial and venous puncture sites, which are usually accessed through a tissue tract.

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique, as described, for example, in William Grossman's "Cardiac Catheterization and Angioplasty," $3^{rd}$ Ed., Lea and Febiger, Philadelphia, 1986, incorporated herein by reference. Vascular access is generally provided through an introducer sheath, which is positioned to extend from outside the patient body into the vascular lumen.

When vascular access is no longer required, the introducer sheath is removed and bleeding at the puncture site stopped. One common approach for providing hemostasis (the cessation of bleeding) is to apply external force near and upstream from the puncture site, typically by manual or "digital" compression. This approach suffers from a number of disadvantages. It is time consuming, frequently requiring one-half hour or more of compression before hemostasis is assured. Additionally, such compression techniques rely on clot formation, which can be delayed until anticoagulants used in vascular therapy procedures (such as for heart attacks, stent deployment, non-optical PTCA results, and the like) wear off. This can take two to four hours, thereby increasing the time required before completion of the compression technique. The compression procedure is further uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation so as to assure continued hemostasis. During this time renewed bleeding may occur, resulting in blood loss through the tract, hematoma and/or pseudo-aneurysm formation, as well as arteriovenous fistula formation. These complications may require blood transfusion and/or surgical intervention.

The incidence of complications from compression induced hemostasis increases when the size of the introducer sheath grows larger, and/or when the patient is anti-coagulated. It is clear that the compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable fasteners or sealing bodies to stop bleeding has previously been proposed. Generally, these approaches rely on the placement of a thrombogenic and bioabsorbable material, such as collagen, at the superficial arterial wall over the puncture site. While potentially effective, this approach suffers from a number of problems. It can be difficult to properly locate the interface of the overlying tissue and the adventitial surface of the blood vessel. Locating the fastener too far from that interface can result in failure to provide hemostasis, and subsequent hematoma and/or pseudo-aneurysm formation. Conversely, if the sealing body intrudes into the artificial lumen, intravascular clots and/or collagen pieces with thrombus attached can form and embolize downstream, causing vascular occlusion. Also, thrombus formation on the surface of a sealing body protruding into the lumen can cause a stenosis, which can obstruct normal blood flow. Other possible complications include infection, as well as adverse reaction to the collagen or other implant.

A more effective approach for vascular closure has been proposed in U.S. Pat. Nos. 5,417,699, 5,613,974; and PCT published Patent Application No. PCT/US96/10271 filed on Jun. 12, 1996, the full disclosures of which are incorporated herein by reference. A suture applying device is introduced through the tissue tract with a distal end of the device extending through the vascular puncture. One or more needles in the device are then used to draw suture through the blood vessel wall on opposite sides of the puncture, and the suture is secured directly over the adventitial surface of the blood vessel wall to provide highly reliable closure.

While a significant improvement over the use of manual pressure, clamps, and collagen plugs, certain design criteria have been found to be important to successful suturing to achieve vascular closure. For example, it is highly beneficial to properly direct the needles through the blood vessel wall at a significant distance from the puncture so that the suture is well anchored in the tissue and can provide tight closure. It is also highly beneficial to insure that the needle deployment takes place when the device is properly positioned relative to the vessel wall. The ease of deployment and efficacy of the procedure can further be enhanced by reducing the cross-section of that portion of the device which is inserted into the tissue tract and/or the vessel itself, which may also allow closure of the vessel in a relatively short amount of time without imposing excessive injury to the tissue tract or vessel.

For the above reasons, it would be desirable to provide improved devices, systems, and methods for suturing vascular punctures. It would be particularly beneficial if these improved devices provided some or all of the benefits while overcoming one or more of the disadvantages discussed above.

2. Description of the Background Art

U.S. Pat. Nos. 5,700,273, 5,836,956, and 5,846,253 describe a wound closure apparatus and method in which needles are threaded with suture inside a blood vessel. U.S. Pat. No. 5,496,332 describes a wound closure apparatus and method for its use, while U.S. Pat. No. 5,364,408 describes an endoscopic suture system.

U.S. Pat. No. 5,374,275 describes a surgical suturing device and method of use, while U.S. Pat. No. 5,417,699 describes a device and method for the percutaneous suturing of a vascular puncture site. An instrument for closing trocar puncture wounds is described in U.S. Pat. No. 5,470,338, and a related device is described in U.S. Pat. Nos. 5,527,321. 5,507,757 also describes a method of closing puncture wounds.

SUMMARY OF THE INVENTION

The present invention provides improved devices, systems, and methods for suturing of body lumens. The device often allows the suturing of vascular puncture sites located at the distal end of a percutaneous tissue tract with greater ease, in less time, and with less patient trauma than known systems. These improvements are generally provided through the use of shafts having smaller cross-sections than prior suturing systems. In the exemplary embodiment, an elongate articulated foot near a distal end of a shaft is inserted through the penetration and actuated so that the foot extends along the lumenal axis. The foot carries suture attachment cuffs, and can be drawn proximally up against the endothelial surface of the blood vessel. Needles are advanced from the shaft, through the vessel wall beyond the penetration, and into engagement with the needle cuffs. The cross-section of the shaft within the tissue tract can be minimized by laterally deflecting the needles before they leave the shaft, while tapered depressions within the foot can help guide the advancing needles into engagement with the cuffs. The cuffs lockingly engage the needles so that the cuffs can be withdrawn proximally along the needle paths through the tissue tract so as to form a loop of suture across the puncture without having to thread the needles directly with the suture inside the blood vessel. The suture loop may be drawn distally from the shaft, proximally from within the blood vessel, or laterally down one of the needle paths, across the puncture, and out the opposing path. Regardless, the articulating foot may be realigned with the shaft and withdrawn proximally through the tissue tract in a small profile configuration. The use of an articulatable foot in combination with lateral deflection of the needles can avoid dilation of the tissue tract, as was often necessary using known puncture closure systems.

In a first aspect, the invention provides a method for suturing a puncture through a vessel wall of a blood vessel. The puncture is disposed within a tissue tract of a patient body, and the method comprises attaching a flexible filament to a first fitting. The first fitting is inserted through the tissue tract and positioned adjacent the vessel wall, and a needle path is formed by advancing a first needle through the vessel wall. The needle is coupled with the first fitting, and the first needle, the first fitting, and at least a portion of the filament are withdrawn through the vessel wall along the needle path.

First and second fittings will often be coupled to the flexible filament, and will generally be positioned so that the puncture is disposed therebetween. The flexible filament will often comprise a suture extending between the first and second fittings, with each fitting being drawn proximally by an associated needle so as to form the suture loop. Alternatively, at least one of the needles may include a detachable tip and may advance a suture distally along the needle path as the needle penetrates through the vessel wall. The flexible filament can again couple the first and second fittings, here allowing both fittings to be withdrawn along a single needle path so that the suture advances down along the first needle path, laterally across the puncture, and then out the other needle path.

Positioning of the fittings is generally effected by articulating an elongate foot within the blood vessel so that the foot extends along the vessel axis. A confirmation lumen may extend along a shaft supporting the foot to ensure that the foot is positioned within the vessel prior to articulation. Once the foot is properly articulated, it can be withdrawn to firmly engage the endothelial layer of the vessel. The foot will preferably include tapering depressions which direct the advancing needle toward the fitting, and the suture or other flexible filament adjacent the fittings will often be releasably restrained within a narrow slot extending from the depression. The suture or other flexible filament and its associated slot will preferably be arranged to avoid entanglement of the advancing needle in the suture, and to ensure that the fitting and suture can be withdrawn proximally as the needle is retracted. An atraumatic, flexible monorail guidebody may extend from the shaft and/or the articulatable foot to facilitate alignment of the foot with the vessel, and also to help provide hemostasis while the knot is tied. A wide variety of foot articulation mechanisms may be provided, with deployment preferably being effected when the foot is disposed entirely within the vessel and using an actuator and foot motion that avoid dilation of the puncture.

In another aspect, the invention provides a method for suturing an opening in a tissue. The method comprises inserting a distal end of a probe through the opening, the probe defining a probe axis. An elongated foot of the probe is articulated so that first and second ends of the foot extend laterally with the opening aligned therebetween. A first needle path is formed from the probe, through the tissue, and to the first end of the foot. A second needle path is formed from the probe, through the tissue, and to the second end of the foot. Suture is advanced along the first and second needle paths to position a suture loop across the opening.

In another aspect, the invention provides a method for suturing a blood vessel. The vessel has a vessel wall, and the method comprises advancing a shaft toward the vessel wall. The shaft has an axis and a plurality of needle guides. A foot is deployed adjacent the vessel wall so that the foot extends laterally from the shaft. A plurality of needles are advanced from the needle guides of the shaft to the foot to form needle paths through the vessel wall. The needle guides deflect the needles laterally so that a needle path width between the needles is greater than a cross-sectional dimension of the shaft. Suture is advanced along the needle paths to position at least one suture loop across the puncture.

In yet another method of the present invention, a blood vessel is sutured through a tissue tract of a patient body. The vessel has a vessel wall, and the method comprises inserting a distal end of a probe through the puncture and into the blood vessel. A first end of the suture is advanced from the probe within the tissue tract, through the vessel wall, and into the vessel. The first end of the suture is withdrawn from the vessel through the vessel wall, and through a bight of the suture to form a loop of suture across the puncture. The first end of the suture and a second end of the suture adjacent the bight are tensioned to detach the bight from the probe and form a knot affixing the loop of suture across the puncture. Advantageously, the bight of suture may be pre-tied before the probe is inserted into the tissue tract, the bight optionally being releasably attached to the probe.

In a device aspect, the invention provides a system for suturing a blood vessel. The vessel has a vessel wall, and the system comprises a needle having a proximal end and a distal end suitable for forming a needle path through the vessel wall. The needle has a recessed engagement surface adjacent the distal end. The system further comprises a flexible filament and a fitting attached to the filament. The fitting has an opening and a tab extending into the opening, the tab securingly engaging the engagement surface when the needle advances through the vessel wall and into the opening, so that the fitting and at least a portion of the filament can be withdrawn proximally along the needle path by the needle.

In a further device aspect, the invention provides a system for suturing a puncture of a blood vessel within a tissue tract. The vessel has a vessel wall and defines an axis, and the system comprises a shaft having a proximal handle and a distal end suitable for insertion along the tissue tract and into the vessel through the puncture. A foot is mounted near the distal end of the shaft. The foot has plurality of needle receptacles extendable laterally from the shaft. A flexible filament extends between the receptacles of the foot. A plurality of needles are advanceable distally and laterally from the shaft, through the vessel wall outside the puncture, and to the receptacles of the foot.

In yet another device aspect, the invention provides a system for suturing a puncture of a blood vessel within a tissue tract. The vessel has a vessel wall, and the system comprises a shaft having a proximal handle and a distal end suitable for insertion along the tissue tract and into the vessel through the puncture. A foot is mounted near the distal end of the shaft. The foot has a first needle receptacle and is articulatable from a small profile configuration to a large profile configuration by actuation of the handle. A first fitting is removably mounted adjacent the first needle receptacle. A filament is coupled to the first fitting. A first needle is advanceable from the shaft to the first needle receptacle on the articulated foot. The first fitting securely engages the first needle so that the secured first fitting and at least a portion of the filament can be drawn through the vessel wall by the first needle.

In a still further device aspect, the invention provides a probe for suturing an opening in a tissue. The probe comprises a shaft having a proximal end and a distal end and defining an axis therebetween. The shaft has a size and configuration suitable for insertion through the opening in the tissue. An elongate foot is movably mounted to the shaft. An actuator extends along the shaft distally to the foot. Movement of the actuator slides the foot axially and pivots the foot from a low profile configuration to a deployed configuration extending laterally from the shaft. A suture is supported by the foot, and a needle is advanceable from the shaft, through the tissue, and to the deployed foot.

BRIEF DESCRIPTION OF THE DRAWINGS

FIGS. 11A-E illustrate an alternative closure system and method for its use in which a first needle advances the suture to the foot, while a second needle engages and withdraws both the first and second suture cuffs, a flexible filament connecting the suture cuffs, and at least a portion of the suture from within the blood vessel so as to complete a pre-tied knot.

DESCRIPTION OF THE SPECIFIC EMBODIMENTS

Figure 1:
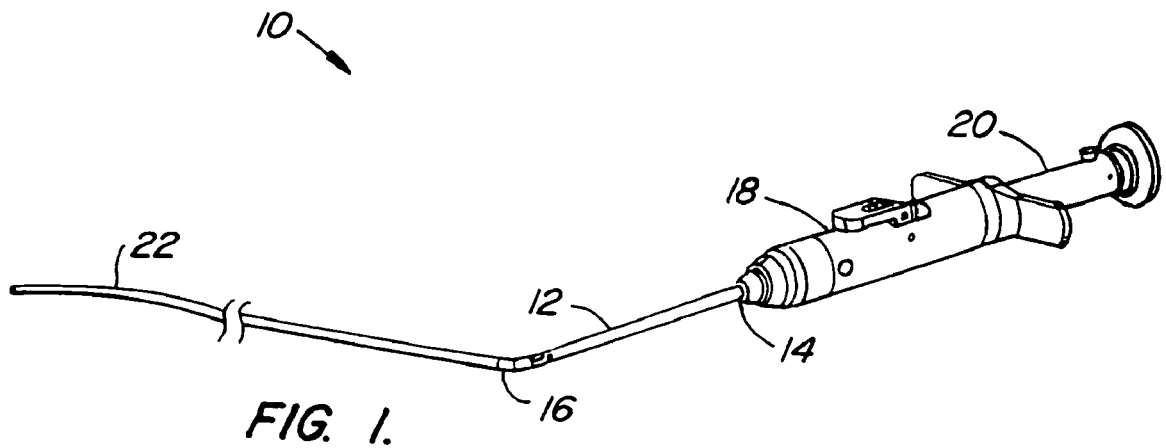
FIG. 1 is a perspective of a percutaneous blood vessel closure device according the principles of the present invention.

Referring now to FIG. 1, a vessel closure device 10 generally has a shaft 12 having a proximal end 14 and a distal end 16. A proximal housing 18 supports a needle actuation handle 20. A flexible, atraumatic monorail guidebody 22 extends distally of distal end 16 of shaft 12.

Figure 2:
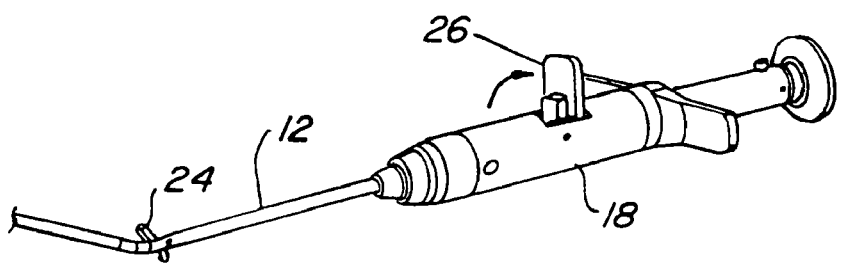
FIG. 2 illustrates the vessel closure device of FIG. 1 in which an elongate foot is shown in a deployed position.

As can be seen with reference to FIG. 2, a foot 24 is articulatably mounted near the distal end of shaft 12. Foot 24 moves between a low profile configuration, in which the foot is substantially aligned along an axis of shaft 12 (as illustrated in FIG. 1), to a deployed position, in which the foot extends laterally from the shaft, upon actuation of a foot actuation handle 26 disposed on proximal housing 18.

Figure 2A:
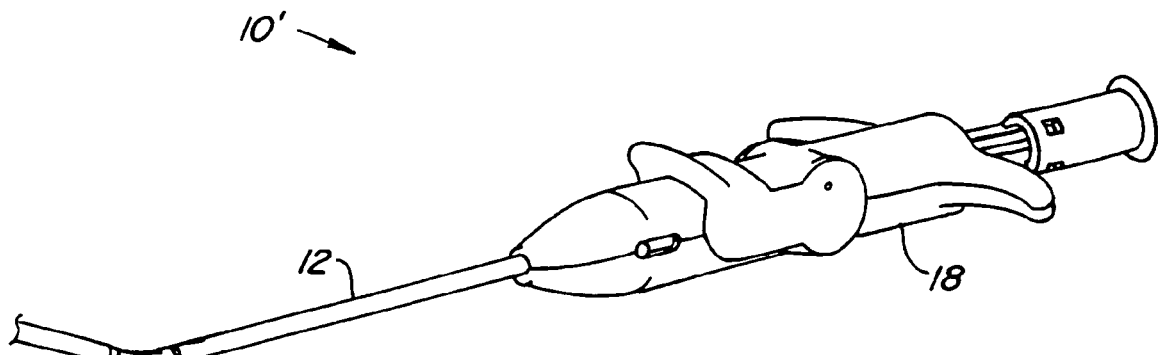
FIGS. 2A-C illustrate actuation of a foot and advancement of needles from a shaft to the articulated foot in a probe similar to the probe of FIG. 1.
Figure 2B:
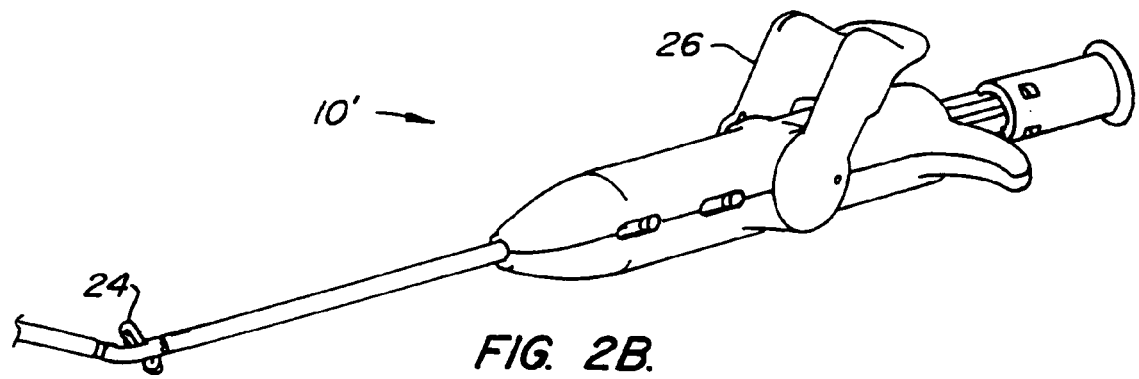
Figure 2C:
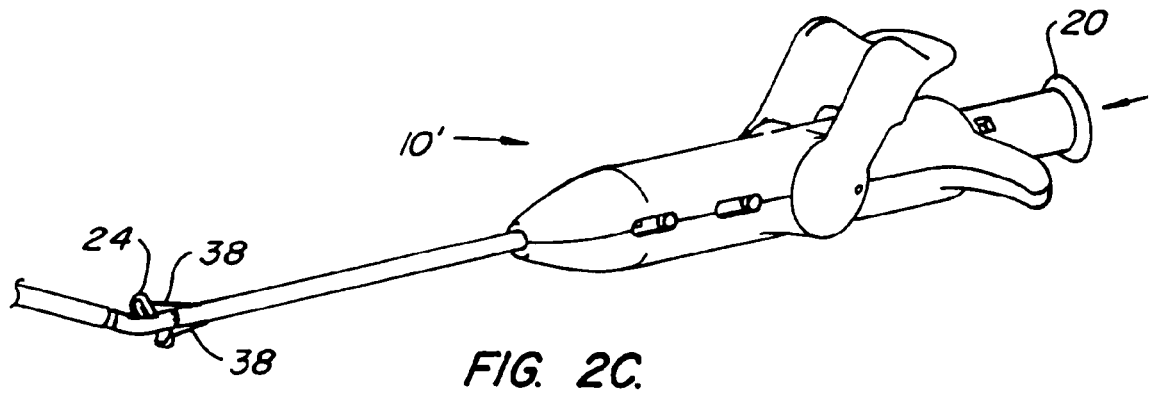

FIGS. 2A through C illustrate the structure and actuation of foot 24 of a preferred probe 10' having a modified proximal housing, and also show how needles 38 can be advanced distally from shaft 12 to the foot by depressing needle actuation handle 20.

Figure 3A:
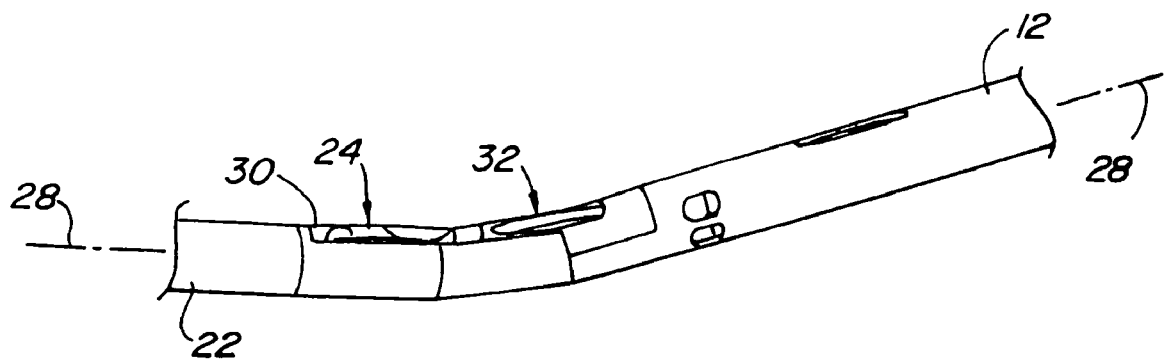
FIG. 3A is a detailed view showing the foot of the vessel closure device of FIG. 1 in a parked position prior to deployment.

Actuation of foot 24 is illustrated more clearly in FIGS. 3A and B. In the parked position illustrated in FIG. 3A, foot 24 extends substantially along axis 28 of shaft 12. Note that the axis of the shaft need not be straight, as the shaft may curve somewhat, particularly adjacent the foot. In the exemplary embodiment, foot 24 is substantially disposed within a foot receptacle 30 of shaft 12 so as to minimize the cross-section of the device adjacent the foot prior to deployment. Advantageously, prior to deployment of the foot, device 10 can have a cross-section adjacent foot 24 of about 7 Fr or less, ideally having a cross-section of about 6 Fr or less for the entire device distally of the proximal end 14 of shaft 12.

Figure 3B:
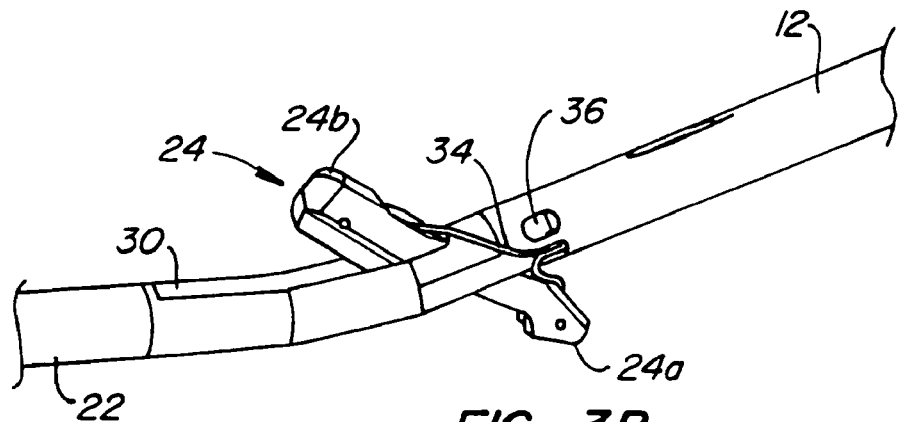
FIG. 3B is a detailed view showing the foot of the vessel closure device of FIG. 1 in a deployed position.

Actuation of foot handle 26 slides a foot actuation wire 32 proximally, pulling foot 24 from a parked position to the deployed position illustrated in FIG. 3B. Once deployed, a first end 24a and a second end 24b of foot 24 extend laterally from the shaft. Suture 34 here comprises a continuous filament with ends disposed in needle receptacles adjacent each end of the foot. An intermediate portion of suture 34 may extend proximally along a suture lumen of shaft 12 to and/or beyond proximal housing 18. Alternatively, in preferred probe 10', the length of suture between the ends may extend distally within flexible guidebody 22, preferably in a dedicated lumen (separate from the monorail guidewire lumen). In still further alternatives described below, a short length of suture or some other flexible filament may extend substantially directly between the needle receptacles.

Shaft 12 also includes a foot position verification lumen that extends distally from a position verification port 36 to a position indicator at housing 18. When the foot is properly positioned within the blood vessel, blood pressure will cause blood to flow proximally through the indicator lumen to the indicator. The indicator may optionally comprise a blood exit port, a clear receptacle in which blood is visible, or the like. In the exemplary embodiment, the indicator of handle 18 comprises a length of clear tubing extending from housing 18 (not shown) in which the blood is clearly visible. It should be understood that a wide variety of alternative position verifications sensors might be used, including electrical pressure sensors, electrolytic fluid detectors, or the like.

Figure 4A:
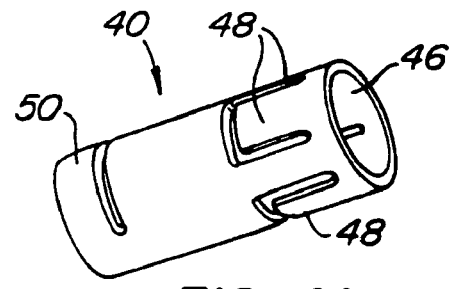
FIGS. 4 and 4A are perspective views illustrating a suture attachment cuff and an associated barbed needle for use in the vessel closure device of FIG. 1.
Figure 4:
Figure 5:
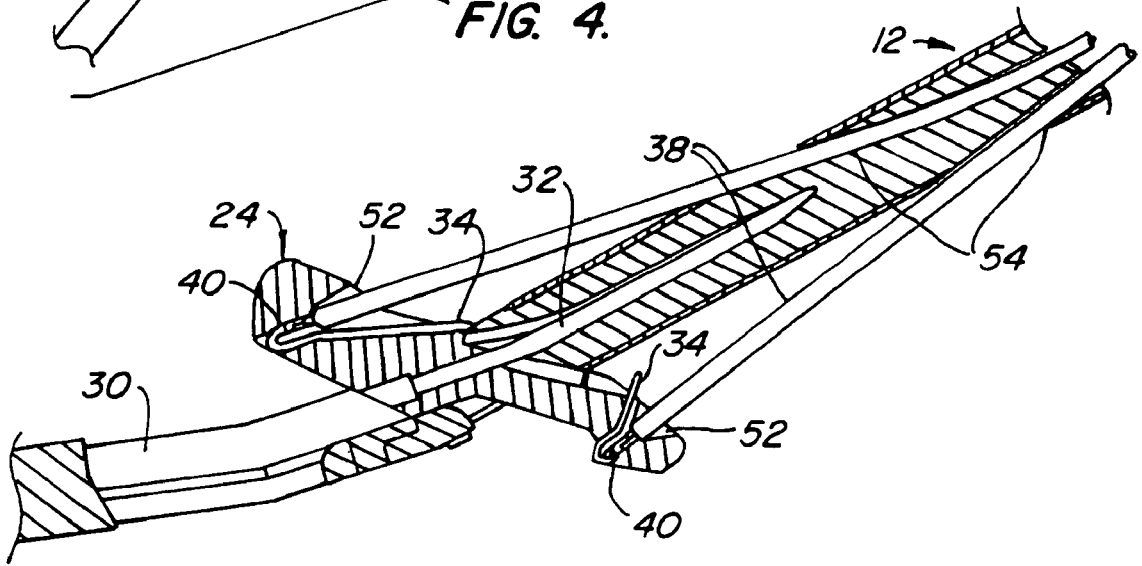
FIG. 5 is a cross-sectional view showing the barbed needles securingly engaging the suture cuffs of the deployed foot.

The structures used in positioning a loop of suture across the puncture can be understood with reference to FIGS. 4, 4A, and 5. In general terms, needles 38 extend from shaft 12 into secured engagement with fittings 40 attached to sutures 34. More specifically, needles 38 include a barbed end 42 defining a recessed engagement surface 44. Fittings 40 are roughly cylindrical structures having an axial channel 46 which receives barbed end 44 of needle 38 therein. A first slot is cut in fitting 44 so as to define at least one tab 48. Tabs 48 can be resiliently biased inward into channel 46. As needle 38 advances into fitting 40, barbed end 42 resiliently displaces tab 48 clear of channel 46 so as to allow the barbed end to pass axially into the fitting. Once barbed end 42 is disposed axially beyond tab 48, the tab resiliently flexes back into the channel, capturing needle 38 by engagement between the tab and recessed surface 44. As each tab can hold the fitting in place on the needle, the use of more than one tab increases the reliability of the system. Ideally, three tabs are provided, as illustrated in FIG. 4A.

To facilitate attachment of fitting 40 to suture 34, a second slot cut in the tubular fitting structure defines a suture attachment collar 50. Optionally, collar 50 may be crimped about suture 34 to mechanically affix the suture to fitting 40. In addition and/or instead of mechanical crimping, suture 34 may be bonded to fitting 40 using an adhesive, heat, fasteners, knots, or the like.

Fitting 40 is quite small in size, and is generally configured to facilitate withdrawing the fitting (and the attached suture) along with needle 38 axially through the vessel wall along the needle path. Needle 38 will generally have a cross-sectional width of between about 0.010 inches and 0.020 inches. Barb 42 will extend laterally so as to define an engagement surface 44 having a protruding length of between about 0.002 inches and 0.005 inches. Fitting 40 will preferably have a cross-sectional size roughly corresponding to or only slightly larger than needle 38. Fitting 40 will typically have an outer lateral width of between about 0.014 inches and 0.025 inches, and an axial length of between about 0.035 inches and 0.050 inches. Channel 46 will be sized to receive at least a portion of needle 38, and will generally have a width of between about 0.010 inches and 0.020 inches. Suture 34 will preferably extend axially opposite the open end of channel 46 so as to minimize drag when the suture is drawn proximally along the needle path. In the exemplary embodiment, needle 38 has a diameter of about 0.020 inches, while the fitting comprises a tube having an outer diameter of about 0.020 inches, an inner diameter of about 0.016 inches, and an overall length of about 0.047 inches. The fitting will typically comprise a resilient material, preferably comprising a metal, and in the exemplary embodiment, comprising stainless steel.

Needles 38 typically have a length of between about 5.0 inches and 6.0 inches, and will preferably be sufficiently stiff to be advanced in compression through the vessel wall (and adjacent tissues) for up to 0.5 inches when supported in cantilever. Nonetheless, the needles will ideally be flexible enough to be laterally deflected within shaft 12, as can be understood with reference to FIG. S. Needles 38 generally comprise a high strength metal, ideally comprising stainless steel. Fittings 40 will also preferably comprise a flexible material to allow tab 48 to flex out of the way of barbed end 42, and to resiliently rebound and engage recessed surface 44. In the exemplary embodiment, barbed end 42 has a diameter of about 0.015 inches, with the diameter of the needle decreasing to about 0.008 inches proximally of the barb so as to define the recessed engagement surface.

As was generally described above, foot 24 includes needle receptacles 52 adjacent the ends of the foot. A fitting 40 (with an associated end of suture 34) is disposed within each needle receptacle, and a surface of the receptacle tapers proximally and outwardly so as to guide the advancing needles 38 into engagement with fittings 40 when foot 24 is in the deployed position. As fittings 40 (and associated portions of suture 34) are releasable supported in the foot, needles 38 can be withdrawn proximally so as to draw the fittings and suture ends from the foot proximally into (and optionally through) shaft 12. The needle receptacles of the exemplary embodiment taper outward at an angle between 20 and 35 degrees from the centerline of fitting 40, and the fitting is held in a recess having a diameter of about 0.0230 inches and a length of about 0.042 inches. A lateral opening or window through the side of foot to the fitting recess may be provided to facilitate needle and/or cuff positioning during assembly of the probe, and a protruding collar near the proximal end of the fitting recess may help keep the fitting in position.

FIG. 5 also illustrates the lateral deflection of needles 38 by needle guides 54 of shaft 12. This lateral deflection of the needles allows the use of a small diameter shaft, while still encompassing sufficient tissue within the suture loop on opposite sides of the puncture so as to effect hemostasis when the suture looped is tightened and secured. In the exemplary embodiment, shaft 12 comprises an outer casing of a biocompatible material such as stainless steel, carbon fiber, nylon, another suitable polymer, or the like. Needle guides 54 may be defined at least in part as lumens formed within the casing of a polymeric material such as nylon or the like. In some embodiments, shaft 12 may comprise a carbon fiber filled nylon, or carbon fiber filled with an alternative material.

Figure 6A:
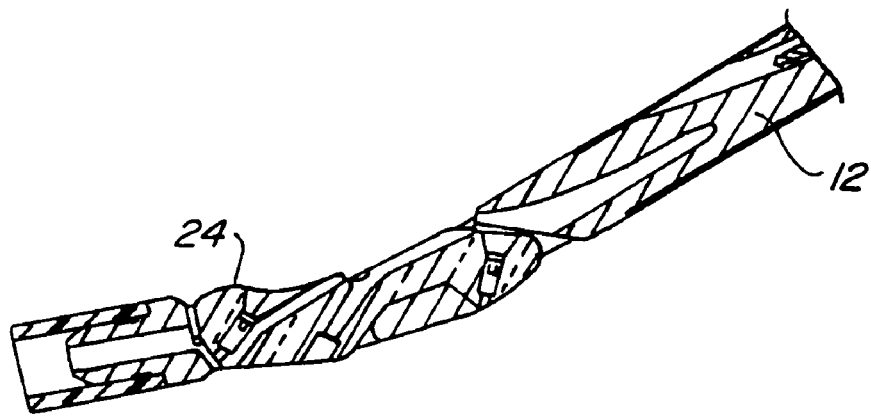
FIGS. 6A-C illustrate one embodiment of a deployable foot, in which the foot slides and pivots when drawn proximally by a tension member.
Figure 6B:
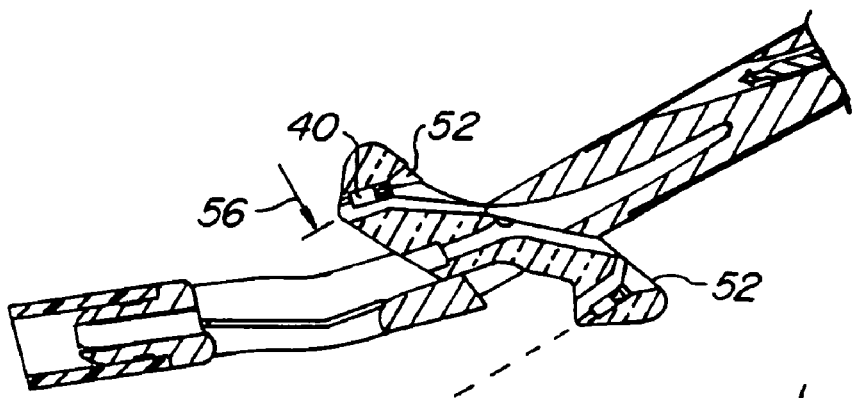
Figure 6C:
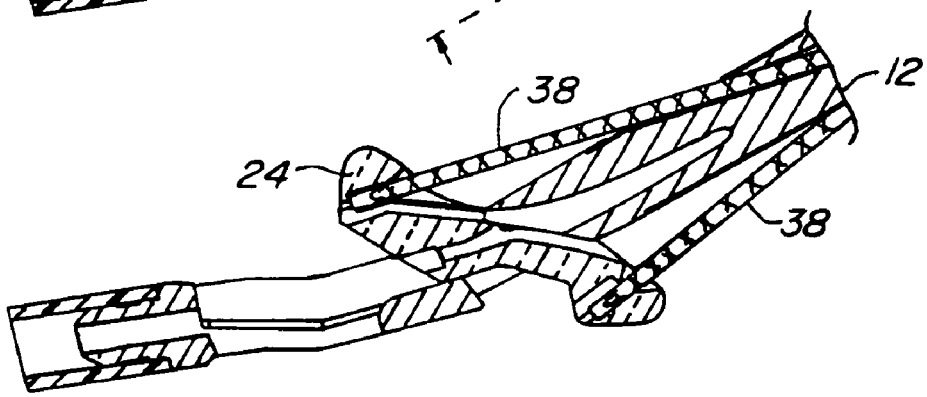

One example of a suitable structure and articulation motion for foot 24 is illustrated in FIGS. 6A and B. Foot actuation wire 32 (see FIG. 3A) rides in a lumen of shaft 12, and draws foot 24 from a parked position (shown in FIG. 6A) to a deployed position (shown in FIG. 6B) through a combination of sliding and pivoting of the foot. The foot remains supported throughout its range of motion by arms disposed laterally on either side of the foot, the arms defining (at least in part) foot receptacle 30. Once foot 24 is deployed, needle receptacles 52 and/or the fittings disposed therein will preferably define a lateral suturing width 56 in a range from about 0.260 inches to about 0.300 inches. Foot 24 may be machined or cast from a polymer or metal, but will preferably comprise a polymer such as carbon fiber filled nylon. In some cases, foot 24 may be molded as two separate halves which can subsequently be affixed together. Needles 38 advance from the fixed needle guides 54, and are laterally directed into fittings 40 by receptacles 52, as illustrated in FIG. 6C. In general, a shape memory alloy such as Nitinol™ in its superelastic regime provides a particularly advantageous actuator wire for manipulating foot 24.

Figure 7:
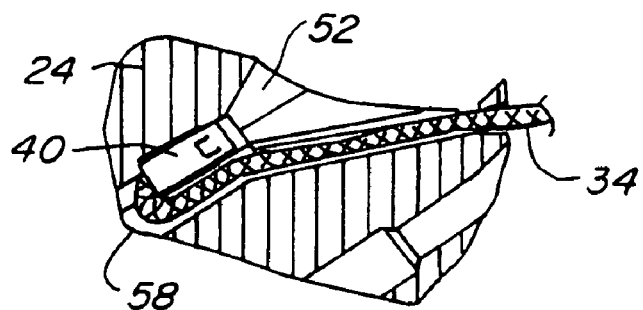
FIG. 7 illustrates the suture cuff positioned within a needle receptacle, and also shows how the suture is releasably secured within a slot extending radially from the needle receptacle.

Referring now to FIG. 7, fittings 40 and suture 34 will be withdrawn proximally by the needles from needle receptacles 52. To releasably support fittings 40 and suture 34 and avoid entanglement of the suture in the needles, suture 34 is fittingly received within a slot 58 which extends laterally from needle receptacles 52. As the needles pull the fitting axially from needle receptacles 52, suture 34 is pulled from slot 58 and free from foot 24. Bending of the suture proximally within the suture slot can also locally increase the suture width, so that the interaction between the bent suture and the slot can help hold the fitting in the recess.

Figure 8A:
FIGS. 8A-C illustrate an alternative foot articulation mechanism in which lateral slots on the foot receive pins from the shaft to allow the foot to pivot and slide axially.
Figure 8B:
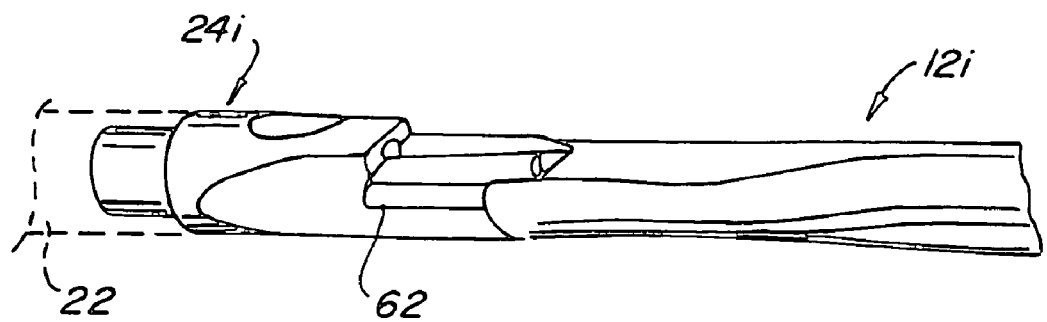
Figure 8C:
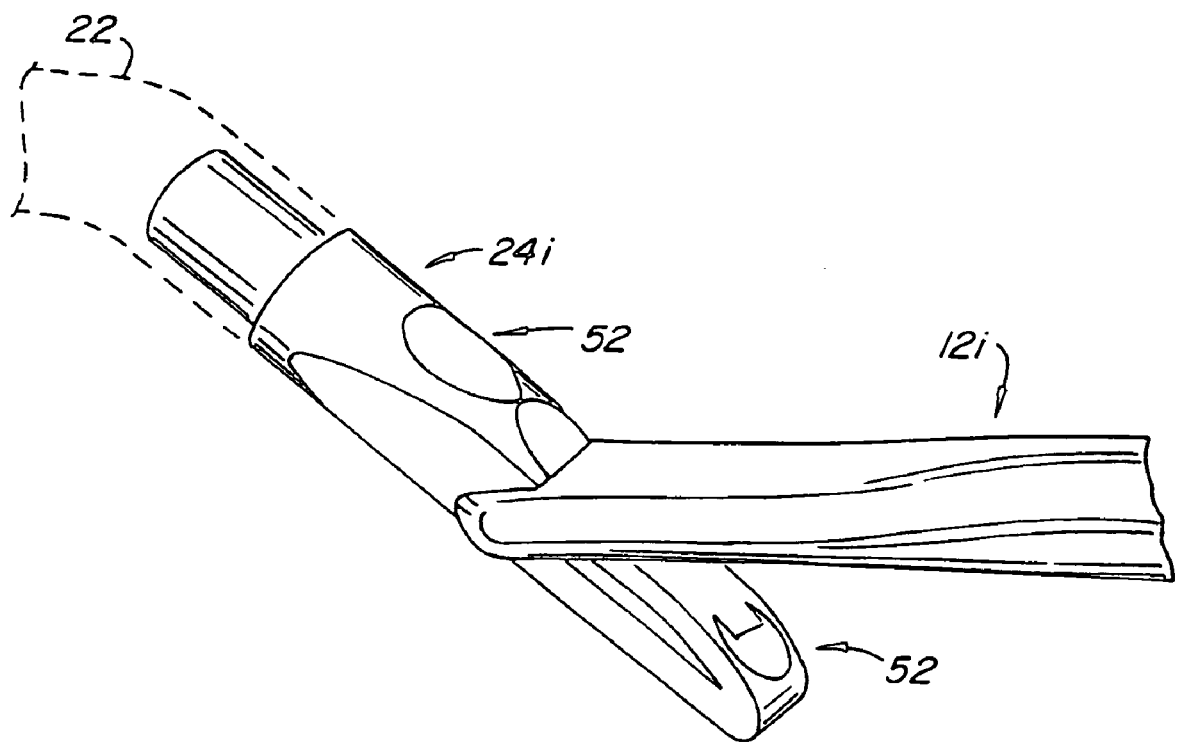

A wide variety of foot actuation mechanisms might be used within the scope of the present invention. A first alternative foot actuation arrangement is illustrated in FIGS. 8A-C. In this embodiment, a shaft 12i has pins 60 which ride in associated slots 62 of a foot 24i. Proximal motion of an actuation wire causes foot 24i to move axially and rotationally, with pins 60 sliding along slot 62, and the foot pivoting about the pins. In this embodiment, guidebody 22 extends directly from the foot, as illustrated in FIG. 8C.

Figure 9A:
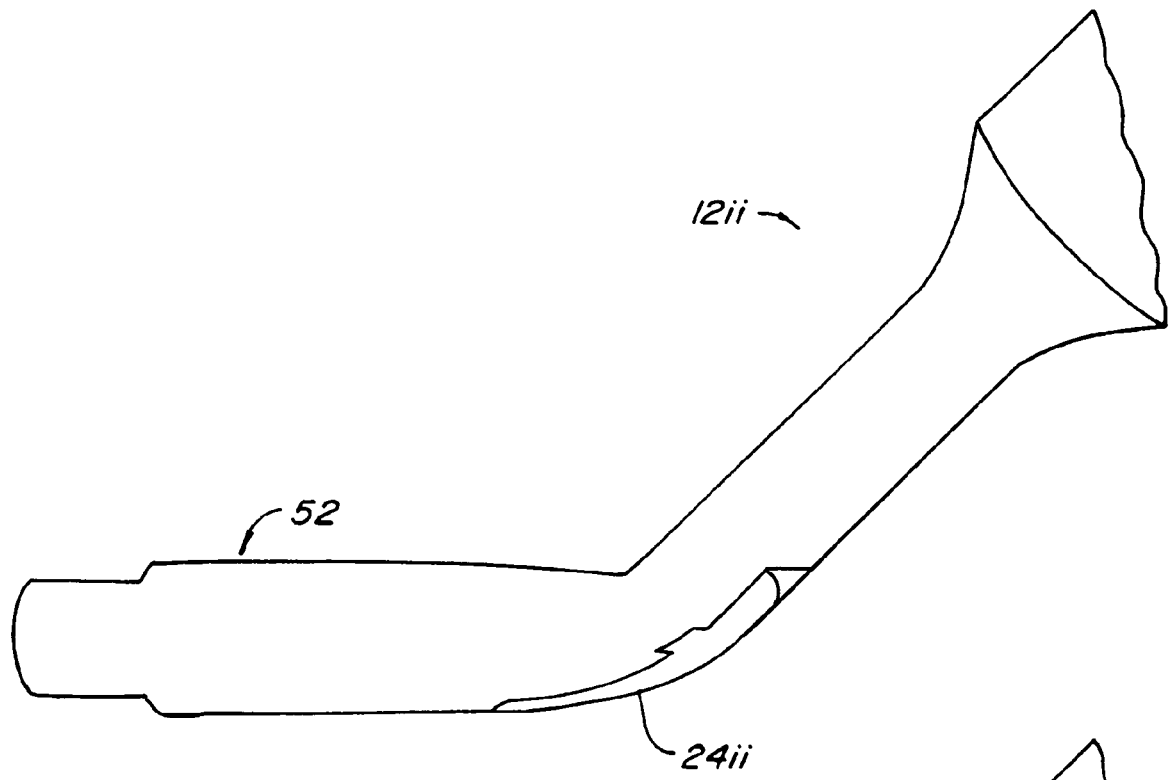
FIGS. 9A and B illustrate a still further alternative foot actuation mechanism in which the foot slides axially within a slot.
Figure 9B:
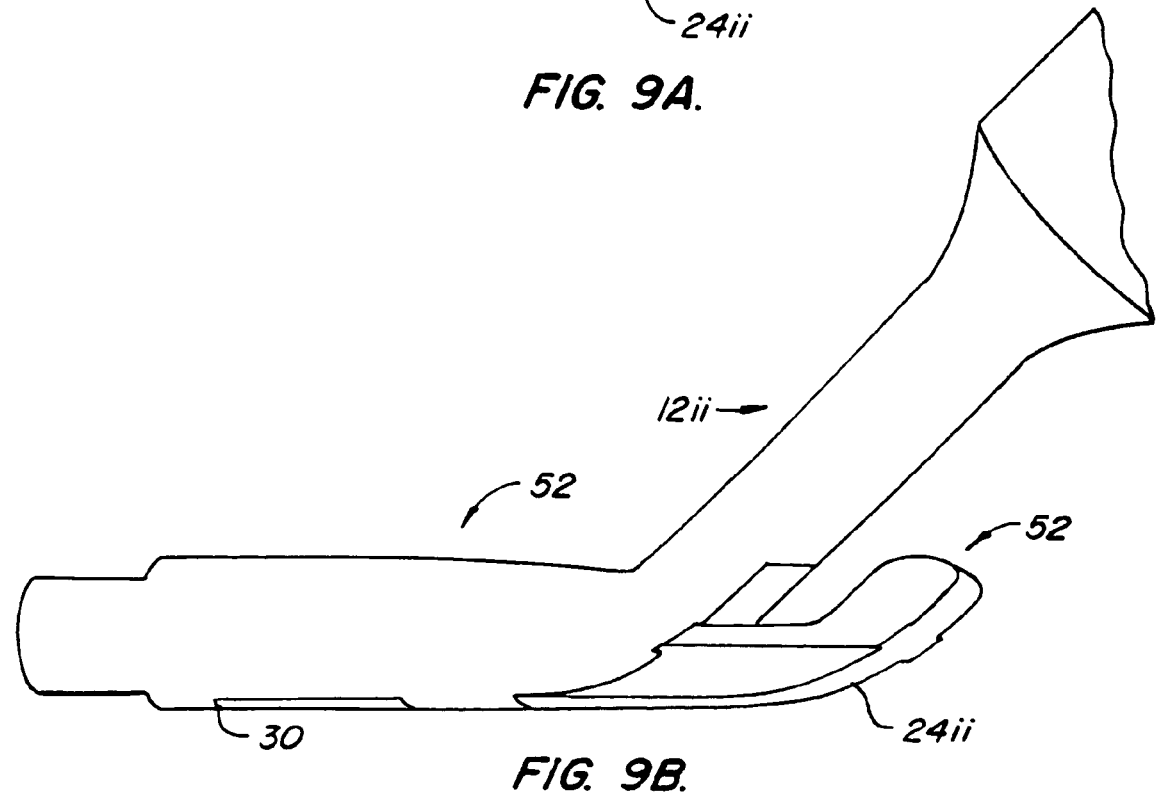
FIGS. 9C and D illustrate a further foot actuation mechanism in which relative movement between the sides of a two-part shaft actuates the foot.

A still further alternative foot actuation mechanism is illustrated in FIGS. 9A and B. In this embodiment, slidable foot 24ii is slidingly received within a receptacle 30 of shaft 12ii. Sliding of the foot 24ii from the parked position of FIG. 9A to the deployed position of FIG. 9B places the needle receptacles 52 in the paths of needles from the shaft 12ii without pivoting of the foot. Guidebody 22 (see FIG. 1) will extend here from a distal end of shaft 12ii at a fixed angle from the shaft. Optionally, insertion through the tissue tract may be facilitated by including an additional bend in the shaft axis adjacent the guidebody on many embodiments.

Yet another foot actuation mechanism can be understood with reference to FIGS. 9C and D. Shaft 12iii is formed in two parts, which slide axially relative to each other when foot actuation lever 26iii moves, using an offset crank arrangement. A similar offset crank supports foot 24iii, so that the sliding shaft parts cause the foot to pivot as shown.

Figure 10A:
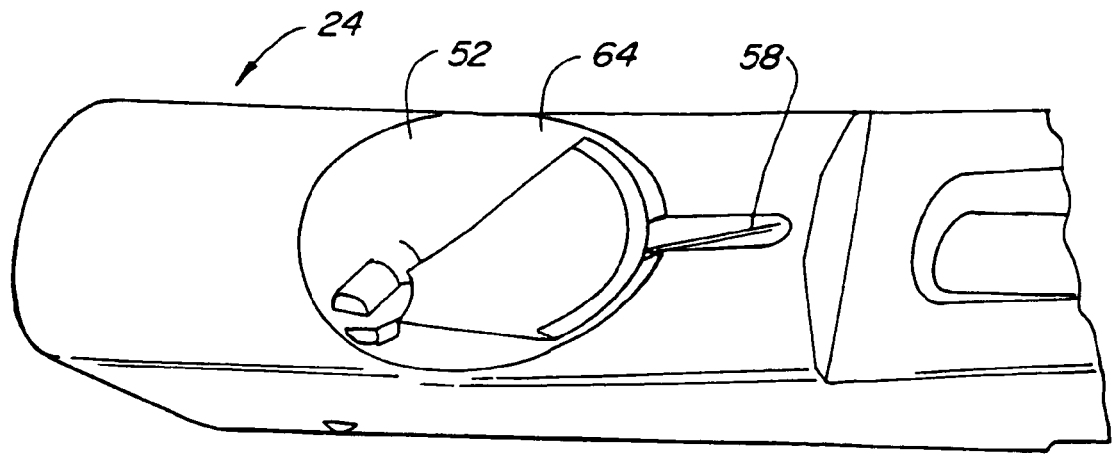
FIGS. 10A-D illustrate alternative structures and techniques for avoiding entanglement of the needle with the suture.
Figure 10B:
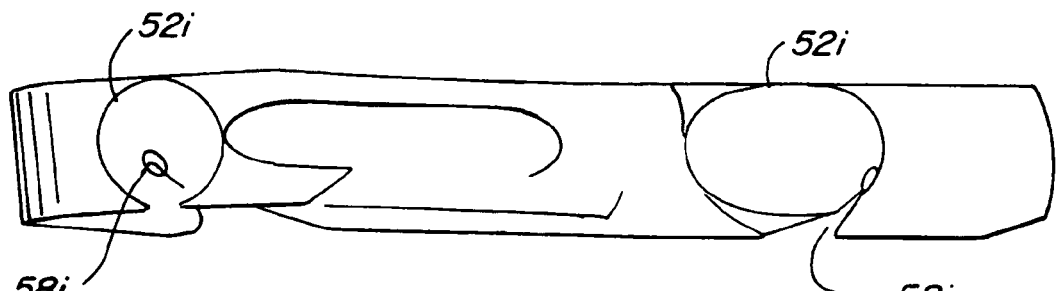

A variety of features may be included in the articulatable foot, the needle receptacle, and/or the needle to avoid tangling of the needle in the suture as the needle is directed to the fitting. As illustrated in FIG. 10A, a moveable flap 64 may extend over slot 58 so that the advancing needle slides along the flap toward the fitting, rather than entering the slot and engaging the suture directly. Flap 64 may be affixed along one side of the slot, with the other side of the flap flexing into the receptacle to release the suture from slot 58 when the fitting and suture are withdrawn by the needle.

An alternative mechanism for avoiding entanglement of the needle with the suture is illustrated 10B. In this embodiment, needle receptacles 52i have tangential slots 58i which extends substantially tangentially to the surface of the receptacle. As a result of this tangential arrangement, a needle entering the receptacle 52i will be directed toward the fitting contained therein, but will generally not be able to enter and advance within the tangential slot 58i so as to become entangled with the suture. As illustrated in this embodiment, the slots may optionally extend laterally through the foot so that the loop of suture can be pulled from one side of the shaft without interference.

Figure 10C:
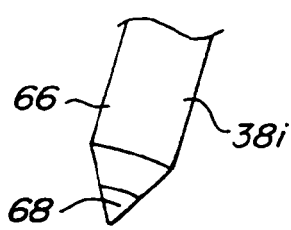
Figure 10D:
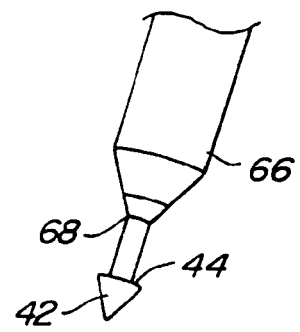

A still further alternative mechanism for avoiding entanglement between the suture and the needle is illustrated in FIGS. 10C and D. Two-part needle 38i includes an outer sheath 66 and an inner core 68. The parts of these needles initially advance together into the receptacles with the needle core 68 withdrawn so that the needle presents a smooth tapered tip (the combined tip preferably being larger in diameter than the slot containing the suture) as illustrated in FIG. 10C. Once two-part needle 38i is fully positioned within the needle receptacle, needle core 68 may extend axially to expose barbed tip 42 and recessed engagement surface 44 and to secure the needle to the fitting within the needle receptacle. In the exemplary embodiment of FIGS. 4 and 5, barbed tip 42 is formed integrally with the rest of the needle structure, but the tip has a larger cross-section than radial slot 58 containing the suture 34. As a result, the barbed tip is unable to enter the slot, thereby avoid entanglement between the needle and suture.

An alternative vessel closure probe 70 will be explained with reference to FIGS. 11A through 11E. This embodiment includes an articulatable foot 24 having a pair of needle receptacles 52, as described above. Although each needle receptacle 52 contains a fitting 40 for coupling a flexible filament to a tip of an associated needle, the filament in this case comprises a short length of suture 74 (or some temporary connecting filament, as shown schematically in phantom in FIG. 11A) spanning directly between the needle receptacles. Rather than pulling the two ends of an extended loop through the needle paths and proximally out the tissue tract for tying, closure system 70 advances a single end of the suture distally along one needle path, across the puncture, and then proximally along the other needle path. To provide this interaction, at least one needle includes means for attaching suture 34 to short suture 74, here in the form of a detachable coupling structure carried on the at least one needle. This structure facilitates the use of a pre-tied knot.

Referring now to FIGS. 11A and B, the distal end of probe 70 advances distally through skin S and into a tissue T of the patient while the probe is in the small profile configuration with foot 24 aligned along the axis of the probe. Here, however, an end 76 of suture 34 is affixed to a detachable needle tip 78 of a hollow needle 38'. Detachable tip 78 comprises a fitting having an opening receiving an end of suture similar to fitting 40, attached to a barbed needle end (similar to that of needle 38). Suture 34 may extend proximally within hollow needle 38 where the needle has an open channel along its length, may exit the hollow needle just proximally of detachable tip 78, or may be disposed alongside a solid needle. Needle 38 (opposite hollow needle 38') has a fixed barbed tip, as described above, and a bight of suture 80 is releasably attached to the probe shaft encircling the opening of needle guide 54 of the fixed tip needle. The bight of suture may be releasably disposed within a slot of the probe, may be temporarily held in place by a weak adhesive or coating, or the like. A second end 82 of suture 34 extends proximally along the shaft of the probe, the second end of the suture optionally also being releasably held along the shaft.

Bight 80 will define a knot when first end suture passes therethrough, as can be understood with reference to FIGS. 11Ai and 11Aii. Bight 80 will often include more than one loop, and may be pre-arranged so as to define a square knot (using the layout schematically illustrated in FIG. 11Ai), a clinch knot (FIG. 11Aii), or a variety of known or new surgical knots.

Probe 70 advances along tissue tract TT to puncture P in blood vessel V. Once foot 24 is disposed within a blood vessel V, a pull wire moves the foot proximally and pivots the foot laterally so that the foot extends along an axis A of the vessel, as illustrated in FIG. 11B. The foot can then be pulled proximally against an inner surface of the vessel wall W to ensure that the needle receptacles 52 are properly positioned.

Figure 11C:
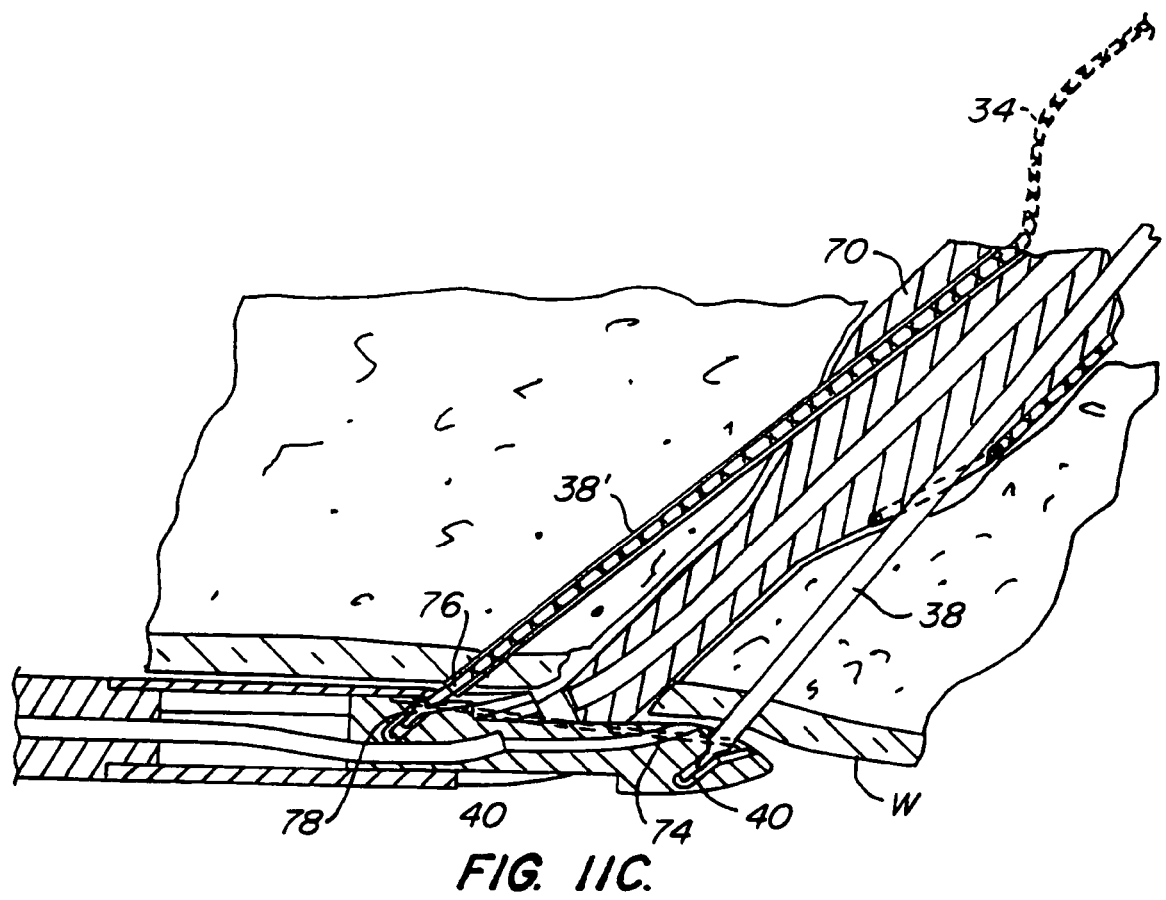

As can be understood with reference to FIGS. 11C and D, hollow needle 38' and needle 38 advance to engage fittings 40 within receptacles 52. Hollow needle 38' draws first end 76 of suture 34 distally through vessel wall W, and detachable tip 78 is secured into an associated fitting 40 using the barb and tab interaction described above. As short suture 74 extends between fittings 40, and as detachable tip 78 can pull free of hollow needle 38' when the needles are withdrawn, this effectively couples needle 38 to first end 76 of suture 34. The detachable tip riding partially within the hollow needle (or vice versa) so that the assembly remains together under compression. Hence, needle 38 can pull the suture distally along the needle path formed by hollow needle 38', across the puncture P, and proximally along the needle path formed by needle 38, as illustrated in FIG. 11D.

Figure 11D:
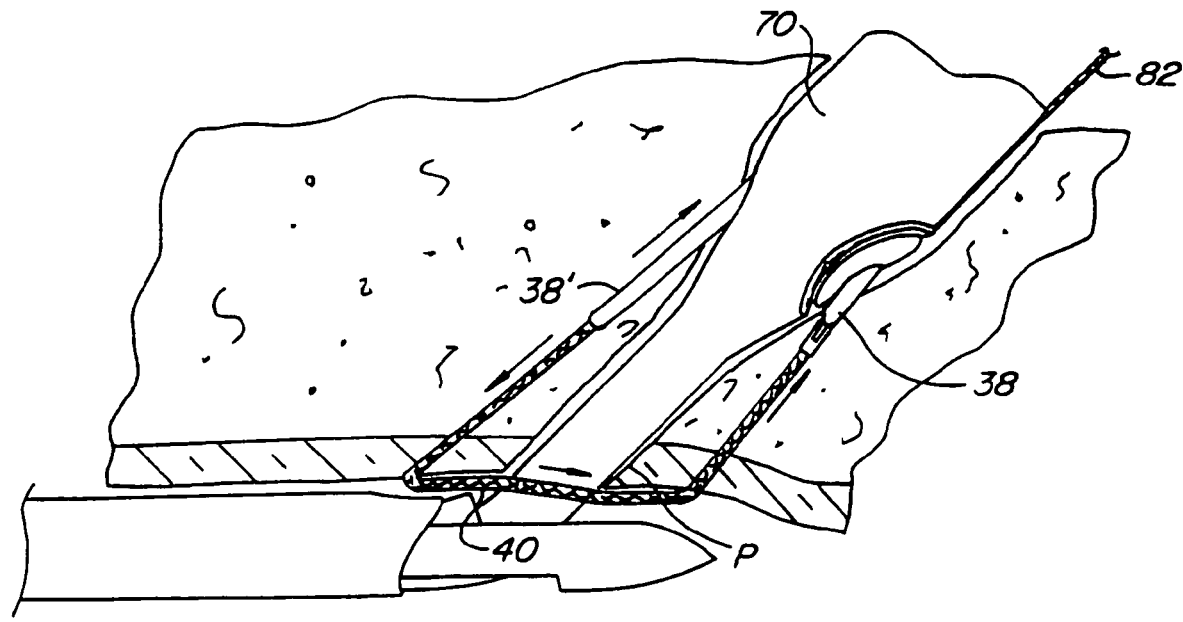
Figure 11E:
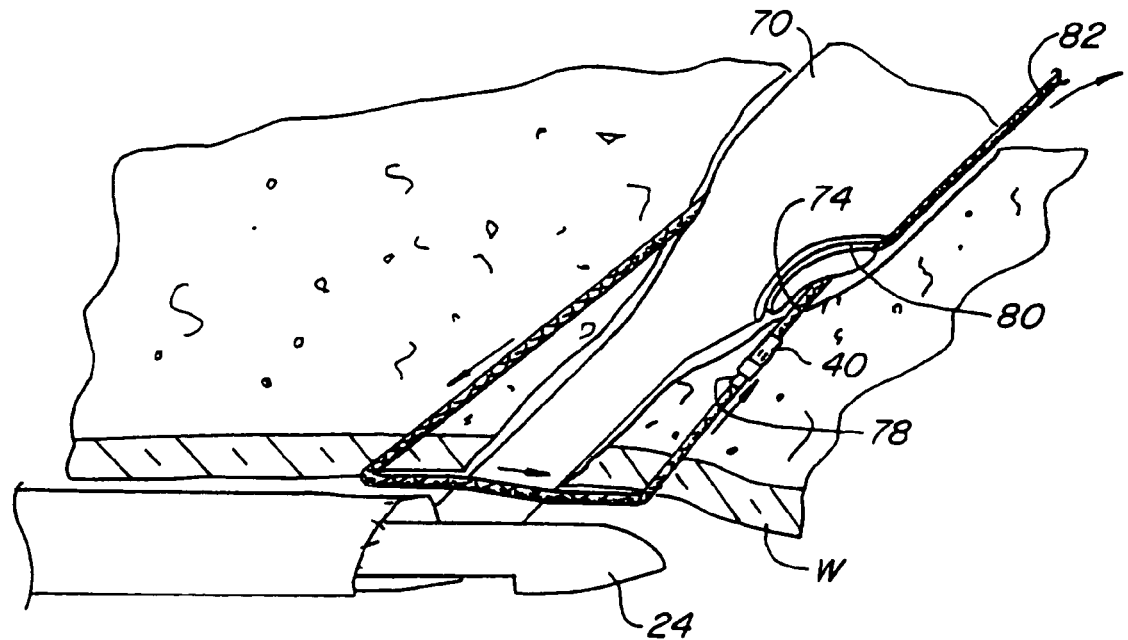

FIGS. 11D and E show that the knot can be completed by pulling needle 38, short suture 74, and second end 76 of suture 34 (together with the fittings 40 and detachable needle tip 78) proximally through bight 80. Second end 82 of suture 34 can be pulled to free bight 80, and the ends of the suture can be tightened and the probe removed to provide permanent hemostasis.

It will be recognized that removal of probe 70 can be facilitated by coupling first end 76 to bight 80 over an outer surface of the probe, and by arranging suture 34 and hollow needle 38' so that the suture can pull free of the needle when detachable tip 78 is released, for example, by having the suture exit the needle proximally of the tip through a channel that extends to the tip so that the needle does not encircle the suture. By including such provisions, after foot 24 is returned to the narrow configuration, the probe can be pulled proximally from the tissue tract leaving the pre-tied knot in place.

Alternative arrangements (using the detachable needle ends of probe 70) are possible to provide the benefit of a pre-tied knot and the like for closure of a vessel puncture. For example, a probe having a pair of needles in which each needle included a detachable tip might be used to pull first end 76 through a bight, so that the bight need not encircle the needle path of one of the needles.

Figure 12A:
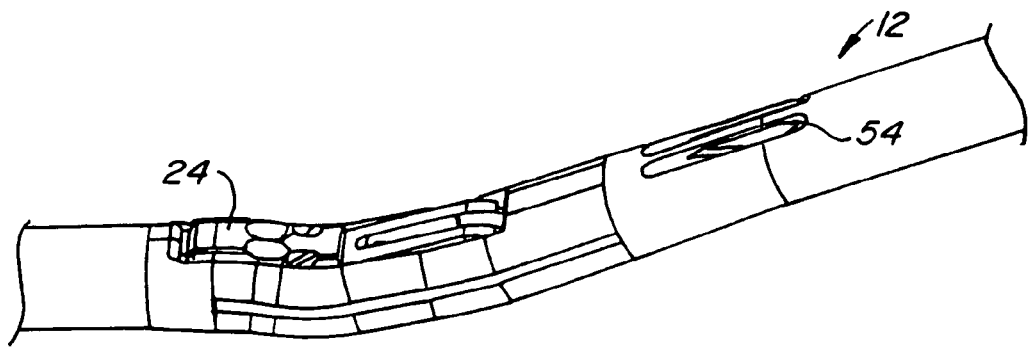
FIGS. 12A and B illustrate an alternative probe having two pairs of needles and a foot with four needle receptacles so as to form two loops of suture across a puncture of a blood vessel.
Figure 12B:
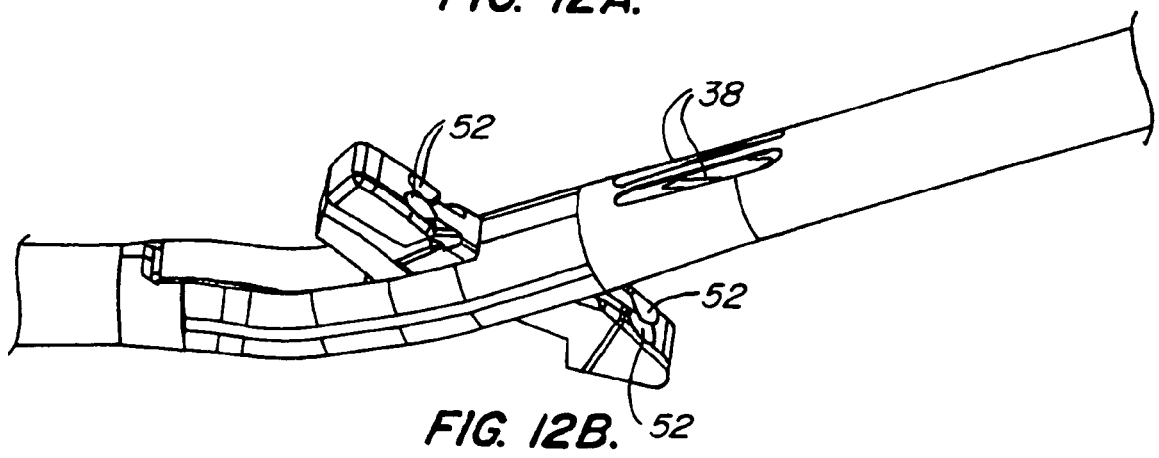

In some cases, particularly for closure of large punctures, it may be advantageous to provide multiple suture loops across the puncture, either in parallel, in an "X" pattern, or the like. As illustrated in FIGS. 12A and B, the present invention encompasses the use of more than two needles and associated receptacles, fittings, sutures, and the like. Multiple loop systems may have four, six, eight, or more needles, or may even have odd numbers of needles and fittings, particularly where one or more fittings have a plurality of suture ends extending therefrom. This allows a wide variety of stitching patterns to be provided by such multiple loop probes.

Figure 13A:
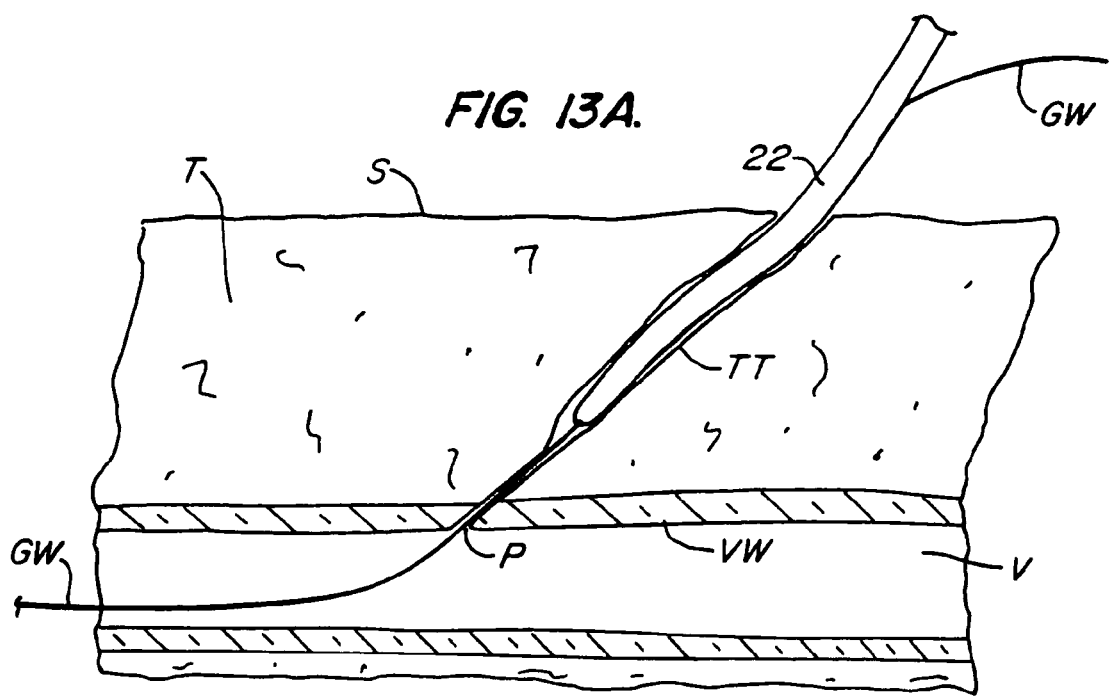
FIGS. 13A-G illustrate a method for use of a suture system so as to effect hemostasis of a blood vessel puncture through a tissue tract.
Figure 13B:
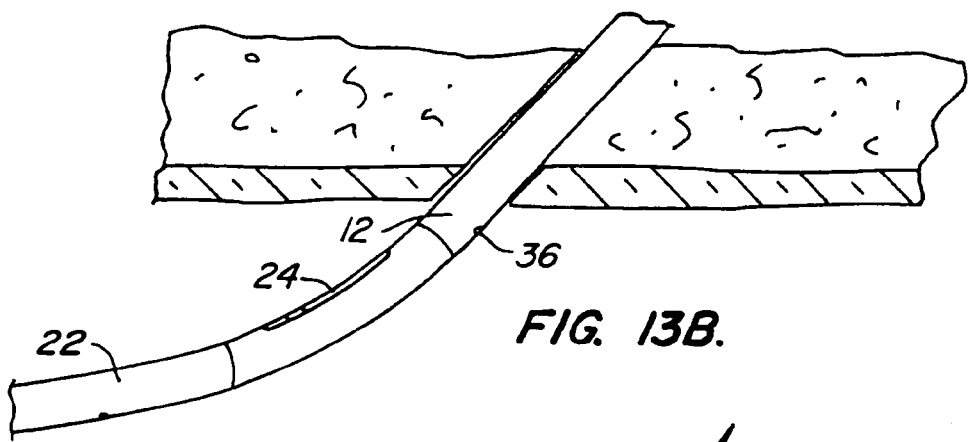

The method of use of the probes of FIGS. 1-7 can be understood with reference to FIGS. 13A-G. After accessing a blood vessel V (often using the Seldinger technique), a guidewire GW is left extending into skin S and down through tissue T along tissue tract TT. Guidewire GW enters vessel V through a puncture P in vessel wall W, and extends along the vessel throughout many endovascular procedures. As illustrated in FIG. 13A, distal guidebody 22 is advanced over the guidewire GW in a monorail fashion, so that the guidewire helps to direct the probe along the tissue tract TT and into the vessel through puncture P. FIG. 13B shows that when sensor 36 is disposed within the vessel, blood can flow from the sensor port and through a lumen in shaft 12 to the proximal handle to notify the operator that foot 24 has been advanced far enough for deployment.

Figure 13C:
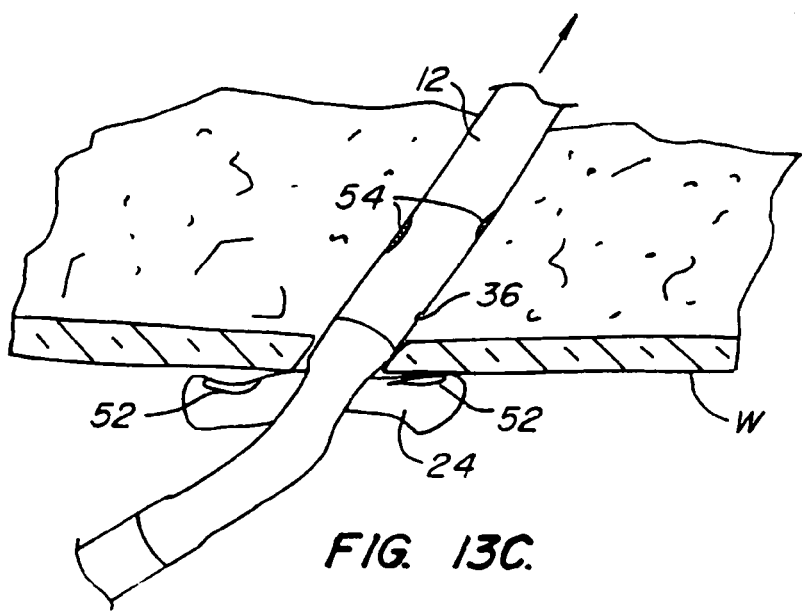

Deployment of the foot is effected by actuation of the foot deployment handle, as described and illustrated above with reference to FIGS. 2 and 2B. As described above, guidebody 22 helps to align the probe with the axis of vessel V. Guidebody 22 may be set at an angle and/or offset relative to shaft 12 as appropriate to aid in alignment with a particular vessel access technique. As shown in FIG. 13C, the deployed foot 24 extends laterally from the shaft, so that foot 24 adjacent receptacles 52 can be drawn up against vessel wall W by gently pulling shaft 12. Hence, the foot helps to accurately position the needle guides 54 at a distance from the vessel wall.

Figure 13D:
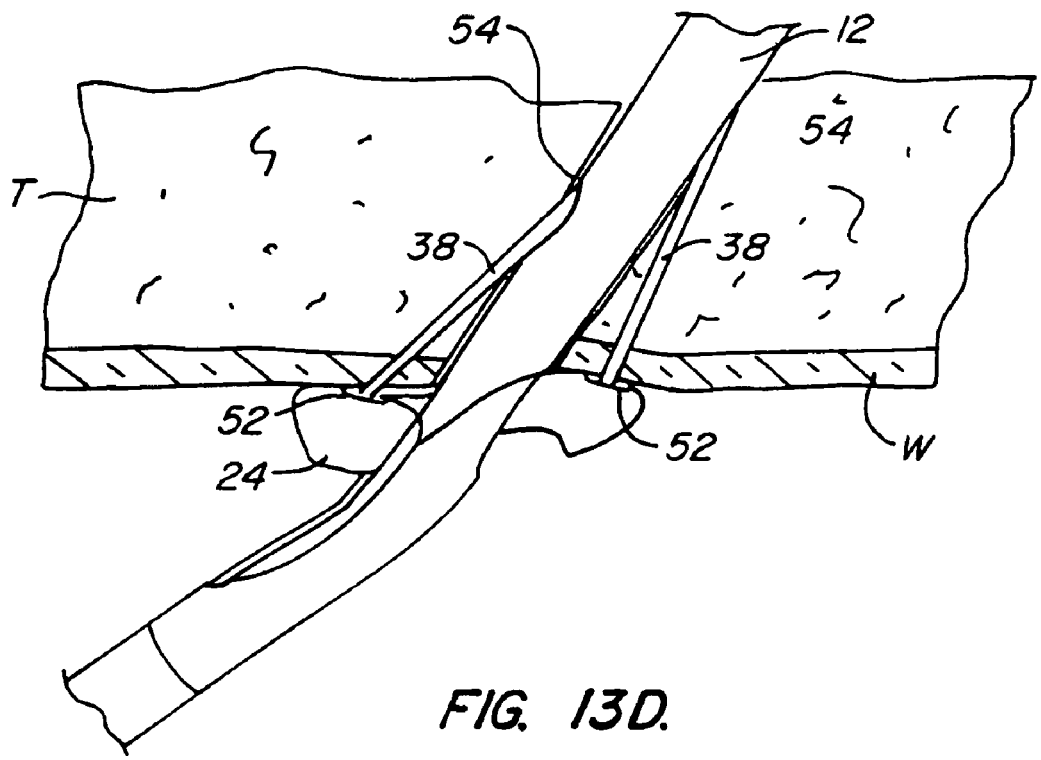

Referring now to FIG. 13D, flexible needles 38 are deflected laterally by needle guides 54 toward receptacles 52 of the deployed foot. As a result, the needles advance in cantilever both distally and laterally when needle actuation handle 20 is pressed (see FIG. 2C), and the tapering surfaces of receptacles 52 help to push the needles back into alignment with the fittings so as to overcome any unintended deflection of the needles by tissue T or vessel wall W. This ensures that needles 38 securingly engage fittings 40 within receptacles 52, thereby coupling the ends of suture 34 to the needles. While suture 34 is here illustrated running along the side of shaft 12 outside foot receptacle 30 to a lumen within guidebody 22, it should be understood that the suture loop might instead extend proximally in a lumen of shaft 12, might be routed through the foot and/or foot receptacle, and/or might be stored in a spool adjacent foot 24. Regardless, suture 34 should able to pull free of the probe between its ends to form a continuous loop across puncture P.

Figure 13E:
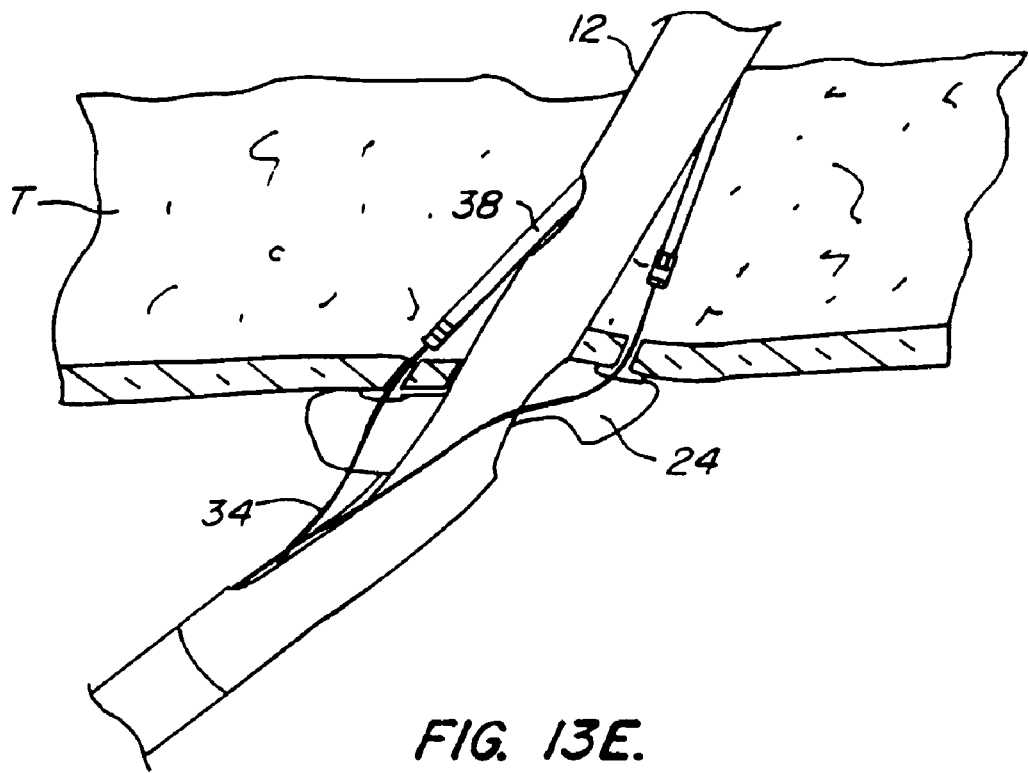
Figure 13F:
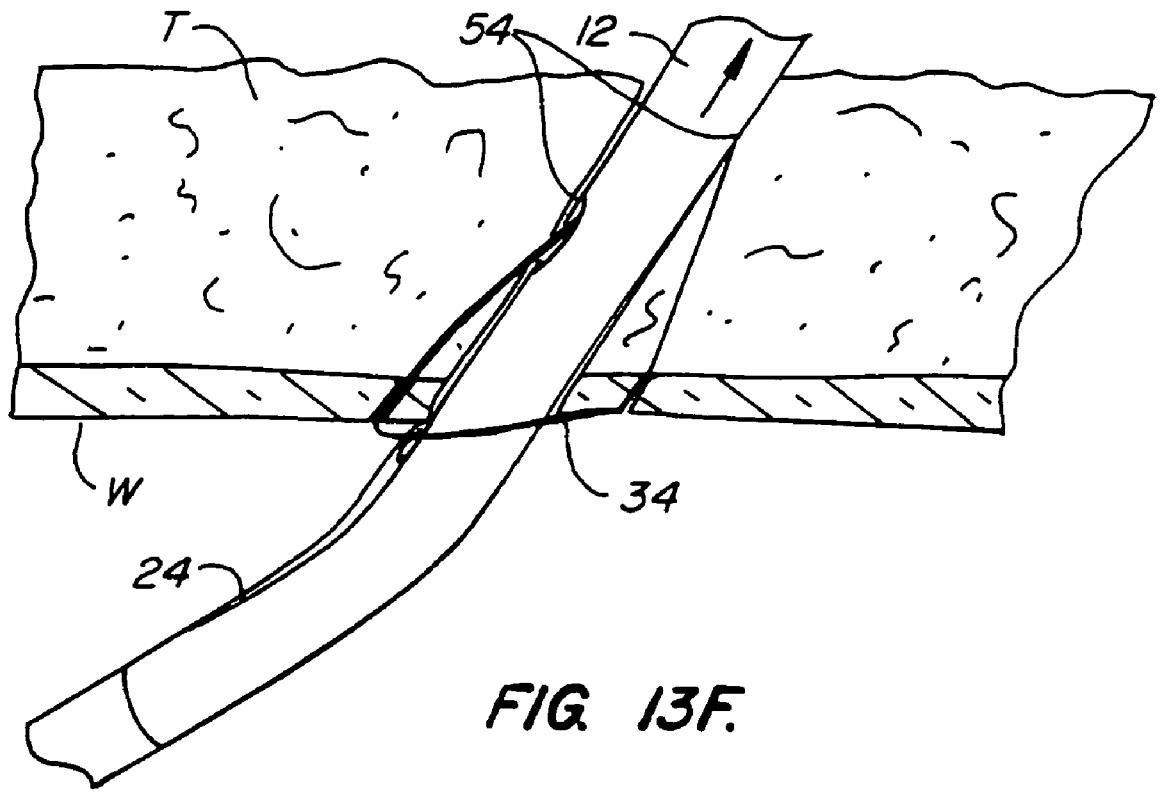

Referring now to FIGS. 13E and F, fittings 40 and the ends of suture 34 are drawn proximally through the vessel wall W along the needle paths formed by needles 38. Optionally, the needles may be withdrawn proximally out of the tissue tract and clear of shaft 12, or they may remain coupled to the shaft within needle guides 54. The foot actuator is moved to store foot 24 along shaft 12, and the shaft can then be pulled proximally from the tissue tract. Guidebody 22, which may comprise a soft, compliant polymer, may temporarily extend at least partially into tissue tract TT and through puncture P to help reduce the loss of blood until the loop is secured.

Figure 13G:
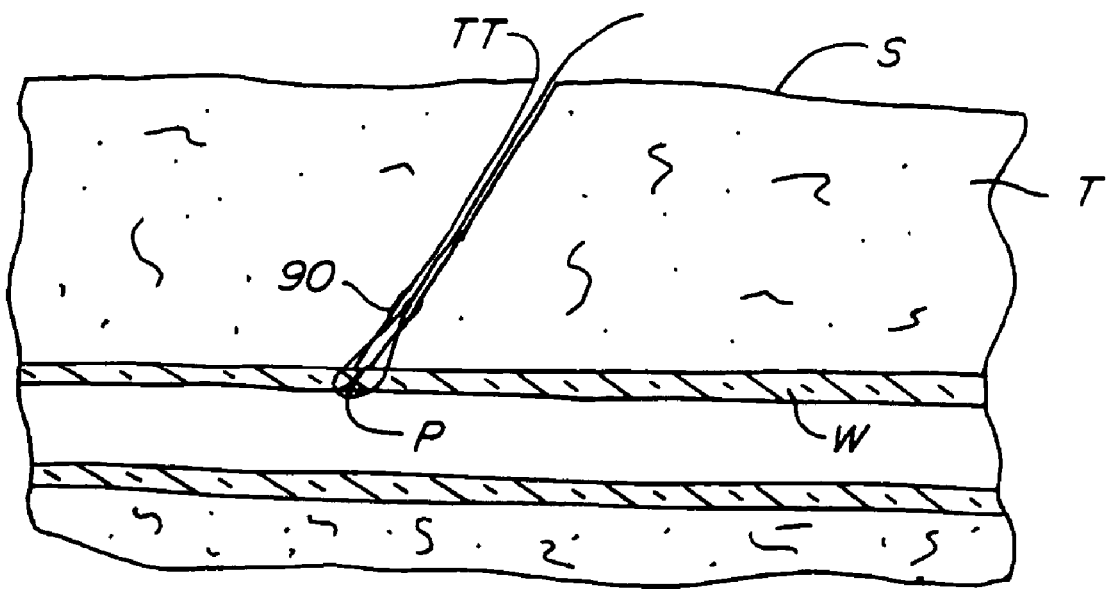

Now referring to FIG. 13G, once shaft 12 has been withdrawn sufficiently to expose needle guides 54, the ends of the suture loop can be grasped by the operator. Tying of a knot in suture 34 can then proceed in a conventional manner. The use of a clinch knot may facilitate gradual tightening of the knot while removing guidebody 22, although a wide variety of knot and knot advancing techniques might be used.

While the exemplary embodiments have been described in some detail for clarity of understanding, a wide variety of modifications, adaptations, and changes will be obvious to those of skill in the art. For example, some of the benefits of the present invention might be provided by actuating a foot disposed outside the blood vessel within the tissue tract, and advancing needles from within the blood vessel proximally through the vessel wall toward the actuated foot. Hence, the scope of the present invention is limited solely by the appended claims.

What is claimed is:

1. A device for closing an opening in a tissue, the device comprising:
   a shaft having a proximal end portion, a distal end portion, and a foot receptacle disposed at the distal end portion;

a foot disposed within the foot receptacle on the distal end portion of the shaft and spaced apart from the proximal end portion, the foot being movable from within the foot receptacle to a deployed position at least in part external to the foot receptacle with the foot extending laterally across the distal end portion of the shaft and from the shaft;

a flexible guidebody coupled to and extending distally from the distal end portion of the shaft beyond the foot receptacle; and a needle advanceable from the shaft through the tissue and to the foot when the foot is moved to the deployed position.

2. The device of claim 1, wherein the flexible guidebody defines a guidewire lumen.

3. The device of claim 2, wherein the flexible guidebody has a distal end, wherein the flexible guidebody defines a guidewire entry port at the flexible guidebody distal end, and wherein the flexible guidebody defines a guidewire exit port situated along the flexible guidebody at a location proximal to the guidewire entry port.

4. The device of claim 3, wherein the guidewire exit port is situated at a location distal to the distal end portion of the shaft.

5. The device of claim 1, wherein a portion of the shaft curves such that the flexible guidebody extends from the shaft at an angle relative to an axis of the shaft.

6. The device of claim 1, further comprising a length of suture supported by the foot, the length of suture having a first end and a second end, wherein the flexible guidebody defines a lumen, and wherein the length of suture between the first end and the second end extends distally within the lumen of the flexible guidebody.

7. The device of claim 1, wherein the tissue is a wall of a blood vessel.

8. A method for closing an opening in a tissue, the method comprising:

providing a shaft having a distal end portion, a proximal end portion, and a foot receptacle disposed at the distal end portion, at least a portion of the foot receptacle passing through the shaft, a flexible guidebody coupled to and extending distally from the distal end portion of the shaft, the shaft having a movable foot disposed within the foot receptacle at the distal end portion of the shaft and spaced apart from the proximal end portion, the foot being movable from within the foot receptacle to a deployed position at least in part external to the foot receptacle with the foot extending laterally across the distal end portion of the shaft and from the shaft;

inserting the flexible guidebody through the opening, the flexible guidebody guiding the shaft to the opening;

moving the foot from a parked position to the deployed position;

forming a needle path from the shaft through the tissue; and advancing a suture through the tissue along the needle path to position a suture loop across the opening.

9. The method of claim 8, further comprising partially withdrawing the flexible guidebody from the opening to reduce a flow of blood through the opening.

10. The method of claim 8, further comprising using a guidewire to guide the flexible guidebody through the opening.

11. The method of claim 8, further comprising: securing the suture loop to close the opening; and fully withdrawing the flexible guidebody from the opening after the suture loop is at least partially secured.

12. The method of claim 8, wherein the tissue is a wall of a blood vessel.

13. A device for closing an opening in a tissue, the device comprising:

a shaft having a proximal end, a distal end, and a foot receptacle disposed at the distal end portion, at least a portion of the foot receptacle passing through the shaft, a portion of the shaft being curved adjacent the distal end;

a foot disposed within the foot receptacle near the distal end of the shaft to minimize a cross-section of the shaft and spaced apart from the proximal end, the foot being movable from within the foot receptacle to a deployed position at least in part external to the foot receptacle with the foot extending laterally across the distal end portion of the shaft and from the shaft and a flexible guidebody coupled to and extending distally from the distal end of the shaft at an angle relative to an axis of the shaft; and a needle advanceable from the shaft through the tissue and to the foot when the foot is in a deployed position.

14. The device of claim 13, wherein the flexible guidebody defines a guidewire lumen.

15. The device of claim 14, wherein the flexible guidebody has a distal end, wherein the flexible guidebody defines a guidewire entry port at the flexible guidebody distal end, and wherein the flexible guidebody defines a guidewire exit port situated along the flexible guidebody at a location proximal to the guidewire entry port.

16. The device of claim 15, wherein the guidewire exit port is situated at a location distal to the distal end of the shaft.

17. The device of claim 13, further comprising a length of suture supported by the foot, the length of suture having a first end and a second end.

18. The device of claim 13, wherein the flexible guidebody defines a suture storage lumen.

19. A method for closing an opening in a tissue, the method comprising:

providing a shaft having a distal end, a proximal end, and a foot receptacle disposed at the distal end portion, at least a portion of the foot receptacle extending through the shaft, a flexible guidebody coupled to and extending distally from the distal end of the shaft, the shaft having a movable foot disposed within the foot receptacle at the distal end of the shaft to minimize a cross-section of the shaft and spaced apart from the proximal end, the foot being movable from within the foot receptacle to a deployed position at least in part external to the foot receptacle with the foot extending laterally across the distal end portion of the shaft and from shaft;

inserting the flexible guidebody through the opening;

partially withdrawing the flexible guidebody from the opening to reduce a flow of blood through the opening;

forming a needle path from the shaft through the vessel wall; and advancing a suture through the vessel wall along the needle path to position a suture loop across the opening.

20. The method of claim 19, further comprising using a guidewire to guide the flexible guidebody through the opening 21. The method of claim 19, wherein the opening in the tissue is accessed through a tissue tract through subcutaneous tissue.

22. The method of claim 19, further comprising: securing the suture loop to close the opening; and fully withdrawing the flexible guidebody from the vessel after the suture loop is at least partially secured.

23. A method for closing an opening in a tissue, the method comprising:

providing a shaft having a distal end, a proximal end, and a foot receptacle disposed at the distal end, at least a portion of the foot receptacle extending through the shaft, a flexible guidebody coupled to and extending distally from the distal end of the shaft, the shaft having a movable foot within the foot receptacle at the distal end of the shaft to minimize a cross-section of the shaft and spaced apart from the proximal end, the foot being movable from within the foot receptacle to a deployed position at least in part external to the foot receptacle within the foot extending laterally across the distal end portion of the shaft and from the shaft;

using a guidewire to guide the flexible guidebody through the opening;

forming a needle path from the shaft through the tissue adjacent the opening; and advancing a suture through the tissue along the needle path to position a suture loop across the opening.

24. The method of claim 23, further comprising partially withdrawing the flexible guidebody from the opening to reduce a flow of blood through the opening.

25. The method of claim 23, further comprising: securing the suture loop to close the opening; and fully withdrawing the flexible guidebody from the vessel after the suture loop is at least partially secured.

26. A method for closing an opening in a vessel wall of a blood vessel, the opening disposed within a tissue tract of a patient body, the method comprising:

providing a shaft having a distal end, a proximal end, and a foot receptacle disposed at the distal end, at least a portion of the foot receptacle extending through the shaft, a foot disposed within the foot receptacle near the distal end of the shaft and spaced apart from the proximal end, the foot being movable from within the foot receptacle to a deployed position at least in part external to the foot receptacle with the foot extending laterally across the distal end portion of the shaft and from the shaft, and a flexible guidebody coupled to and extending from the distal end of the shaft, wherein a portion of the shaft has a curve such that the flexible guidebody extends from the shaft at an angle relative to an axis of the shaft;

inserting the flexible guidebody through the opening into the vessel such that the flexible guidebody is positioned coaxially within the vessel and the shaft is positioned coaxially within the tissue tract;

forming a needle path from the shaft through the vessel wall; and advancing a suture through the vessel wall along the needle path to position a suture loop across the opening.

27. The method of claim 26, wherein the foot is movable from a parked position to a deployed position, wherein the foot is aligned with the vessel when in the deployed position.

28. The method of claim 26, further comprising partially withdrawing the flexible guidebody from the vessel to reduce a flow of blood through the opening.

29. The method of claim 26, further comprising using a guidewire to guide the flexible guidebody through the opening and into the blood vessel.

30. The method of claim 26, further comprising: securing the suture loop to close the opening; and fully withdrawing the flexible guidebody from the vessel after the suture loop is at least partially secured.

* * * * *